US007553816B2

(12) United States Patent
Senter et al.

(10) Patent No.: US 7,553,816 B2
(45) Date of Patent: Jun. 30, 2009

(54) *P*-AMIDOBENZYLETHERS IN DRUG DELIVERY AGENTS

(75) Inventors: Peter D. Senter, Seattle, WA (US); Brian E. Toki, Everett, WA (US); Scott Jeffrey, Snohomish, WA (US)

(73) Assignee: Seattle Genetics, Inc., Bothell, WA (US)

( * ) Notice: Subject to any disclaimer, the term of this patent is extended or adjusted under 35 U.S.C. 154(b) by 510 days.

(21) Appl. No.: 10/252,947

(22) Filed: Sep. 23, 2002

(65) Prior Publication Data

US 2003/0130189 A1 Jul. 10, 2003

Related U.S. Application Data

(63) Continuation-in-part of application No. 09/963,103, filed on Sep. 24, 2001, now Pat. No. 7,091,186.

(51) Int. Cl.
*C07K 5/06* (2006.01)
(52) U.S. Cl. .................. 514/19; 530/330; 530/331
(58) Field of Classification Search ............... None
See application file for complete search history.

(56) References Cited

U.S. PATENT DOCUMENTS 6,413,507 B1 * 7/2002 Bentley et al. ............ 424/78.02

FOREIGN PATENT DOCUMENTS

EP 0624377 * 11/1994

OTHER PUBLICATIONS

Ghosh et al. 'Nature of Linkage Between Cationic Headgroups and Cholesteryl Skeleton Controls Gene Transfection Efficiency,' FEBS Letters. vol. 473, pp. 341-344. 2000.*
Rudinger, J. (1976). Peptide Hormones (ed. J.A. Parsons). University Park Press. Baltimore. pp. 1-7.*
Dermer, Gerald. "Another Anniversary for the War on Cancer." Bio/Technology, vol. 12. Mar. 1994.*
Gura, Trisha. "Systems for Identifying New Drugs are Often Faulty." Science, vol. 278, pp. 1041-1042. Nov. 1997.*
Golden, Fredrick. "Of Mice and Men: Don't Blame the Rodents" Time, pp. 44. May 18, 1998.*
Bradely et al. "Limits of Cooperativeity in a Structurally Modular Protein: Response of the Notch Ankyrin Domain to Analogus Alanine Substitutions in Each Repeat." J. Mol. Biol. vol. 324, 202, pp. 373-386.*
de Groot et al., 2002, "Design, Synthesis, and Biological Evaluation of a Dual Tumor-Specific Motive Containing Integrin-targeted Plasmin-cleavable Doxorubicin Prodrug," *Molecular Cancer Therapeutics* 1:901-911.
de Groot et al., 2001, "Elongated Multiple Electronic Cascade and Cyclization Spacer Systems in Activatible Anticancer Prodrugs for Enhanced Drug Release," *J. Org. Chem.* 66(26):8815-8830.
Dubowchik et al., 1997, "Monomethoxytrityl (MMT) as a Versatile Amino Acid Protecting Group for Complex Prodrugs of Anticancer Compounds Sensitive to Strong Acids, Bases and Nucleophiles", *Tetrahedron Letters* 38(30):5257-5260.

Dubowchik et al., 2002, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", *Bioconjugate Chem.* 13:855-869.
International Search Report issued in connection with International application No. PCT/US02/30282, filed Jun. 27, 2004.
Carl et al., 1981, "A novel connector linkage applicable in prodrug design", J. Med. Chem. 24:479-480.
Carl et al., 1980, "Protease-activated 'prodrugs' for cancer chemotherapy", Proc. Natl. Acad. Sci. USA 77:2224-2228.
Chakravarty et al., 1983, "Plasmin-activated prodrugs for cancer chemotherapy. 1. Synthesis and biological activity of peptidylacivicin and peptidylphenylenediamine mustard", J. Med. Chem. 26:633-638.
Chakravarty et al., 1983, "Plasmin-activated prodrugs for cancer chemotherapy. 2. Synthesis and biological activity of peptidyl derivatives of doxorubicin", J. Med. Chem. 26:638-644.
Davidson et al., 1997, "The inhibition of matrix metalloproteinase enzymes", Chemistry & Industry, Apr. 7, 1997, p. 258-261.
de Groot et al., 2000, "Synthesis and biological evaluation of 2'-carbamate-linked and 2'-carbonate-linked prodrugs of paclitaxel: selective activation by the tumor-associated protease plasmin", J. Med. Chem. 43:3093-3102.
de Groot et al., 1999, "Synthesis and biological evaluation of novel prodrugs of anthracyclines for selective activation by the tumor-associated protease plasmin", J. Med. Chem. 42:5277-5283.
Demchik and Sloane, 1999, "Cell-surface proteases in cancer", in: *Proteases : New Perspectives*, Turk, ed., Birkhäuser Verlag, Basel, Switzerland, pp. 109-124.
Denmeade et al., 1998, "Enzymatic activation of a doxorubicin-peptide prodrug by prostate-specific antigen", Cancer Res. 58:2537-2540.
Dubowchik and Walker, 1999, "Receptor-mediated and enzyme-dependent targeting of cytotoxic anticancer drugs", Pharmacol. Therapeut. 83:67-123.
Dubowchik and Firestone, 1998, "Cathepsin B-sensitive dipeptide prodrugs. 1. A model study of structural requirements for efficient release of doxorubicin", Bioorg. Med. Chem. Lett. 8:3341-3346.
Dubowchik et al., 1998, "Cathepsin B-sensitive dipeptide prodrugs. 2. Models of anticancer drugs paclitaxel (Taxol®), mitomycin C and doxorubicin", Bioorg. Med. Chem. Lett. 8:3347-3352.
Greenwald et al., 1999, "Drug delivery systems employing 1,4- or 1,6-elimination: poly(ethylene glycol) prodrugs of amine-containing compounds", J. Med. Chem. 42:3657-3667.
Harada et al., 2000, "Determinants for the drug release from T-0128, camptothecin analogue-carboxymethyl dextran conjugate", J. Controlled Release 69:399-412.

(Continued)

*Primary Examiner*—Anish Gupta
(74) *Attorney, Agent, or Firm*—Mark Sandbaken; Roxanne Holmes

(57) ABSTRACT

Compounds of the formulas

L-[A$_n$-Z-X—W$_w$-]D and B-[Z-X—W$_w$-]D wherein: D is a drug moiety; L is a ligand; B is a blocking group; A is an optional acyl unit; Z is an amino acid or a peptide; X is an aminobenzyl ether self-immolative spacer group; W is an optional second self-immolative group; n is an integer of 0 or 1; and w is an integer of 0 or 1, and compositions of said compounds with pharmaceutically acceptable carrier, diluent and/or excipient, and methods of delivery the drug D via the compounds.

51 Claims, 6 Drawing Sheets

OTHER PUBLICATIONS

Loadman et al., 1999, "Pharmacokinetics of PK1 and doxorubicin in experimental colon tumor models with differing responses to PK1", Clin. Cancer Res. 5:3682-3688.

Mai et al., 2000, "Cell surface complex of cathepsin B/annexin II tetramer in malignant progression", Biochim. Biophys. Acta 1477:215-230.

Niculescu-Duvaz et al., 1999, "Self-immolative anthracycline prodrugs for suicide gene therapy", J. Med. Chem. 42:2485-2489.

Putnam et al., 1996, "Intracellularly biorecognizable derivatives of 5-fluorouracil", Biochem. Pharmacol. 52:957-962.

Senter et al., 1996, "The role of rat serum carboxylesterase in the activation of paclitaxel and camptothecin prodrugs", Cancer Res. 56:1471-1474.

Teicher and Sartorelli, 1980, "Nitrobenzyl halides and carbamates as prototype bioreductive alkylating agents", J. Med. Chem. 23:955-960.

Ueda et al., 1995, "Novel, water-soluble phosphate derivatives of 2'-ethoxycarbonylpaclitaxel as potential prodrugs of paclitaxel: synthesis and antitumor evaluation", Bioorg. Med. Chem. Lett. 5:247-252.

Wakselman, 1983, "1,4- and 1,6-eliminations from hydroxy- and amino-substituted benzyl systems: chemical and biochemical applications", Noveau J. de Chimie 7:439-447.

Kumar et al., "Structural and Dynamic Aspects of Non-Intercalative (1:1) Binding of a Thiazole-Lexitropsin to the Decadeoxyribonucleotide d-[CGCAATTGCC]$_2$; An $^1$H-NMR and Molecular Modeling Study," *Journal of Biomolecular Structure & Dynamics* 9(1):001-021 (1991).

Matsuba et al., "A novel synthetic DNA mino grovve binder, MS-247: antitumor activity and cytotoxic mechanism," *Cancer Chemother. Pharmacol.* 46:1-9 (2000).

White et al., "On the pairing rules for recognition in the minor groove of DNA by pyrrole-imidazole polyamides," *Chemistry & Biology* 4(8):569-578 (1997).

Marchini et al., "α-Bromoacryloyl derivative of distamycin A (PNU 151807): a new non-covalent minor groove DNA binder with antineoplastic activity," *British Journal of Cancer* 80(7):991-997 (1999).

Toki et al., Protease-mediated Fragmentation of p-Amidobenzyl Ethers: A New Strategy for the Activation of Anticancer Prodrugs, J. Org. Chem. 2002 67:1866-1872.

* cited by examiner (VIIa) CBI conjugated to an MGB (VIIb) CPI conjugated to an MGB (VIIc) CPyI conjugated to an MGB (VIId) U-76,073

(VIIe) seco-adozelesin (VIIf) bizclesin (VIIg) CBI-TMI (VIIh) duocarmycin C2 (X=Cl)
(VIIi) duocarmycin B2 (X=Br)

(VIIj) seco-CC-1065

(VIIIa) etoposide (VIIIb) combretastatin A-4

(VIIIc) pancratistatin (VIIId) carminomycin (VIIIe) streptonigrin (VIIIf) zorubicin (VIIIg) elliptinium acetate (VIIIh) mitoxantrone (VIIIj) phenol mustard (VIIIi) daunorubicin (VIIIk) doxorubicin (VIIIl) SN-38

P-AMIDOBENZYLETHERS IN DRUG DELIVERY AGENTS

This application is a continuation-in-part of U.S. application Ser. No. 09/963,103, filed Sep. 24, 2001, now U.S. Pat. No. 7,091,186 the disclosure of which is incorporated herein by reference in its entirety.

1. FIELD OF THE INVENTION

The invention is in the field of pharmaceuticals, and provides drug conjugates as prodrugs for the delivery of drugs to cell populations, where the prodrugs are metabolized and activated by endogenous enzymes to provide active drugs.

2. BACKGROUND OF THE INVENTION

Metastatic carcinomas often express proteolytic enzymes including the cysteine protease cathepsin B (Demchik, L. L.; Sloane, B. F. Cell-Surface Proteases in Cancer. In *Proteases: New Perspectives*; A. Turk, Ed.; Birkhauser Verlag: Basel, 1999; pp 109-124; Mai, J.; Waisman, D. M.; Sloane, B. F. Cell Surface Complex of Cathepsin B/Annexin II Tetramer in Malignant Progression. *Biochim. Biophys. Acta* 2000, 1477, 215-230; Koblinski, J. E.; Ahram, M.; Sloane, B. F. Unraveling the Role of Proteases in Cancer. *Clin. Chim. Acta* 2000, 291, 113-135), matrix metalloproteinases such as collagenases and stromelysins (Davidson, A. H.; Drummond, A. H.; Galloway, W. A.; Whittaker, M. The Inhibition of Matrix Metalloproteinase Enzymes. *Chem. Industry* 1997, 258-261), and serine proteases, represented by plasminogen activator and plasmin (Andreasen, P. A.; Egelund, R.; Petersen, H. H. The Plasminogen Activation System in Tumor Growth, Invasion, and Metastasis. *Cell. Mol. Life Sci.* 2000, 57, 25-40). These enzymes are thought to be critically involved in the events that lead to metastasis, since they are capable of degrading the basement membranes and extracellular matrices around tumor tissues, allowing the tumor cells to migrate and invade into the surrounding stroma and endothelium. Additional activities associated with these proteases include participation in protease cascades, activation of enzymes and growth factors, and in tumor angiogenic stimulation.

Several investigators have explored the possibility of exploiting tumor-associated proteases for the development of new cancer chemotherapeutics. This has led to several promising orally active protease inhibitors having both preclinical and clinical antitumor activities (Davidson, A. H.; Drummond, A. H.; Galloway, W. A.; Whittaker, M. The Inhibition of Matrix Metalloproteinase Enzymes. *Chem. Industry* 1997, 258-261). An additional line of research involves the conscription of proteases for anticancer prodrug activation. Towards this end, peptide-containing anticancer prodrugs have been developed that are activated by proteases within solid tumors (Dubowchik, G. M.; Walker, M. A. Receptor-Mediated and Enzyme-Dependent Targeting of Cytotoxic anticancer Drugs. *Pharm. Ther.* 1999, 83, 67-123; Carl, P. L.; Chakravarty, P. K.; Katzenellenbogen, J. A.; Weber, M. J. Protease-Activated "Prodrugs" for Cancer Chemotherapy. *Proc. Natl. Acad. Sci. USA* 1980, 77, 2224-2228; Chakravarty, P. K.; Carl, P. L.; Weber, M. J.; Katzenellenbogen, J. A. Plasmin-Activated Prodrugs for Cancer Chemotherapy. 1. Synthesis and Biological Activity of Peptidylacivicin and Peptidylphenylenediamine Mustard. *J. Med. Chem.* 1983, 26, 633-638; Chakravarty, P. K.; Carl, P. L.; Weber, M. J.; Katzenellenbogen, J. A. Plasmin-Activated Prodrugs for Cancer Chemotherapy. 2. Synthesis and Biological Activity of Peptidyl Derivatives of Doxorubicin. *J. Med. Chem.* 1983, 26, 638-644; Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341-3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347-3352; de Groot, F. M. H.; de Bart, A. C. W.; Verheijen, J. H.; Scheeren, H. W. Synthesis and Biological Evaluation of Novel Prodrugs of Anthracyclines for Selective Activation by the Tumor-Associated Protease Plasmin. *J. Med. Chem.* 1999, 42, 5277-5283; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093-3102; Greenwald, R. B.; Pendri, A.; Conover, C. D.; Zhao, H.; Choe, Y. H.; Martinez, A.; Shum, K.; Guan, S. Drug Delivery Systems Employing 1,4- or 1,6-Elimination: Poly(ethylene glycol) Prodrugs of Amine-Containing Compounds. *J. Med. Chem.* 1999, 42, 3657-3667; Putnam, D. A.; Shiah, J. G.; Kopecek, J. Intracellularly Biorecognizable Derivatives of 5-Fluorouracil. *Biochem. Pharm.* 1996, 52, 957-962; Harada, M.; Sakakibara, H.; Yano, T; Suzuki, T.; Okuno, S. Determinants for the Drug Release from T-0128, Camptothecin Analogue-Carboxymethyl Detran Conjugate. *J. Cont. Rel.* 2000, 69, 399-412; Denmeade, S. R.; Nagy, A.; Gao, J.; Lilja, H.; Schally, A. V.; Isaacs, J. T. Enzymatic Activation of a Doxorubicin-Peptide Prodrug by Prostate-Specific Antigen. *Cancer Res.* 1998, 58, 2537-2540; Loadman, P. M.; Bibby, M. C.; Double, J. A.; Al-Shakhaa, W. M.; Duncan, R. Pharmacokinetics of PK1 and Doxorubicin in Experimental Colon Tumor Models With Differing Responses to PK1. *Clin. Cancer Res.* 1999, 5, 3682-3688). Several of these agents have led to significant in vitro and in vivo antitumor activities.

There are two general approaches for attaching drugs to peptides for intratumoral proteolytic activation. In the first approach, the drug is appended directly to the peptide, leading to prodrugs that can either release the parent drug or release a drug that contains vestiges of the bound peptide (Putnam, D. A.; Shiah, J. G.; Kopecek, J. Intracellularly Biorecognizable Derivatives of 5-Fluorouracil. *Biochem. Pharm.* 1996, 52, 957-962; Harada, M.; Sakakibara, H.; Yano, T; Suzuki, T.; Okuno, S. Determinants for the Drug Release from T-0128, Camptothecin Analogue-Carboxymethyl Detran Conjugate. *J. Cont. Rel.* 2000, 69, 399-412; Denmeade, S. R.; Nagy, A.; Gao, J.; Lilja, H.; Schally, A. V.; Isaacs, J. T. Enzymatic Activation of a Doxorubicin-Peptide Prodrug by Prostate-Specific Antigen. *Cancer Res.* 1998, 58, 2537-2540). In the latter case, the released drug may have impaired cytotoxic activity. An additional consideration for direct drug attachment to peptides is the negative influence the drug can have on the kinetics of peptide hydrolysis.

To circumvent these potential shortcomings, a second approach has been developed that relies on the use of self-immolative spacers to separate the drug from the site of enzymatic cleavage. The incorporated spacer allows for the release of fully active, chemically unmodified drug from the conjugate upon amide bond hydrolysis. A commonly used spacer utilizes the bifunctional p-aminobenzyl alcohol group, which is linked to the peptide through the amine moiety, thereby forming an amide bond. Amine-containing drugs are attached through carbamate functionalities to the benzylic hydroxyl group of the p-aminobenzyl alcohol-based spacer. The resulting prodrugs are activated upon protease-mediated cleavage, leading to a 1,6-elimination reaction (Wakselman, M. 1,4- and 1,6-Eliminations from Hydroxy- and Amino-Substituted Benzyl Systems: Chemical and Biochemical Applications. *Nouveau J. Chim.* 1983, 7, 439-447) that splits off unmodified drug and carbon dioxide.

This methodology, based on the work of Sartorelli, Katzenellenbogen and coworkers (Teicher, B. A.; Sartorelli, A. C. Nitrobenzyl Halides and Carbamates as Prototype Bioreductive Alkylating Agents. *J. Med. Chem.* 1980, 23, 955-960; Carl, P. L.; Chakravarty, P. K.; Katzenellenbogen, J. A. A Novel Connector Linkage Applicable in Prodrug Design. *J. Med. Chem.* 1981, 24, 479-480) has been applied to plasmin catalyzed release of phenylenediamine mustard (Chakravarty, P. K.; Carl, P. L.; Weber, M. J.; Katzenellenbogen, J. A. Plasmin-Activated Prodrugs for Cancer Chemotherapy. 1. Synthesis and Biological Activity of Peptidyla-civicin and Peptidylphenylenediamine Mustard. *J. Med. Chem.* 1983, 26, 633-638) and anthracyclines (Chakravarty, P. K.; Carl, P. L.: Weber, M. J.; Katzenellenbogen, J. A. Plasmin-Activated Prodrugs for Cancer Chemotherapy. 2. Synthesis and Biological Activity of Peptidyl Derivatives of Doxorubicin. *J. Med. Chem.* 1983, 26, 638-644; de Groot, F. M. H.; de Bart, A. C. W.; Verheijen, J. H.; Scheeren, H. W. Synthesis and Biological Evaluation of Novel Prodrugs of Anthracyclines for Selective Activation by the Tumor-Associated Protease Plasmin. *J. Med. Chem.* 1999, 42, 5277-5283; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093-3102) from their corresponding peptide-p-amidobenzyl carbamate derivatives, and also to release doxorubicin and mitomycin C from peptide-p-amidobenzyl carbamate peptide derivatives by lysosomal enzymes and cathepsin B (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341-3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347-3352; Greenwald, R. B.; Pendri, A.; Conover, C. D.; Zhao, H.; Choe, Y. H.; Martinez, A.; Shum, K.; Guan, S. Drug Delivery Systems Employing 1,4- or 1,6-Elimination: Poly(ethylene glycol) Prodrugs of Amine-Containing Compounds. *J. Med. Chem.* 1999, 42, 3657-3667). The same linkage system has also been applied for the activation of anthracyclines in cells that were transfected with carboxypeptidase G2 (Niculescu-Duvaz, I.; Niculescu-Duvaz, D.; Fiedlos, F.; Spooner, R.; Martin, J.; Marais, R.; Springer, C. J. Self-Immolative Anthracycline Prodrugs for Suicide Gene Therapy. *J. Med. Chem.* 1999, 42, 2485-2489).

The chemistry used for drug attachment has generally been restricted to amine-containing drugs, with the exception of paclitaxel, which was linked through carbonates derived from hydroxyl groups at the 2' or 7-position (Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347-3352; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093-3102). Unlike many carbonates that are hydrolytically unstable, these paclitaxel 2' and 7-carbonates were quite stable in aqueous environments, consistent with what had already been reported for other paclitaxel carbonates (Ueda, Y; Matiskella, J. J.; Mikkilineni, A. B.; Farina, V.; Knipe, J. O.; Rose, W. C.; Casazza, A. M.; Vyas, D. M. Novel, Water-Soluble Phosphate Derivatives of 2'-Ethoxy Carbonylpaclitaxel as Potential Prodrugs of Paclitaxel: Synthesis and Antitumor Evaluation. *Bioorg. Med. Chem. Letts.* 1995, 5, 247-252; Senter, P. D.; Marquardt, H.; Thomas, B. A.; Hammock, B. D.; Frank, I. S.; Svensson, H. P. The Role of Rat Serum Carboxylesterase in the Activation of Paclitaxel and Camptothecin Prodrugs. *Cancer Res.* 1996, 56, 1471-1474). Many drugs containing reactive hydroxyl groups would not be expected to exhibit such high carbonate stability.

The present invention recognizes and addresses the need for broadly useful and versatile methodologies for attaching drugs, including anticancer drugs, to self-immolative spacers, which would lead to high serum stability and conditional drug release upon peptide bond hydrolysis.

The recitation of any reference in Section 2 of this application is not an admission that the reference is prior art to this application.

3. SUMMARY OF THE INVENTION

In one aspect, the present invention provides compositions and methods which may be utilized to target a drug-ligand conjugate (prodrug) to a selected cell population, such as tumor sites, where the prodrug is enzymatically activated to release the drug. Based upon one aspect of the invention described herein, many drugs containing reactive hydroxyl groups may be converted into a prodrug form and in particular may be converted into a prodrug form capable of targeting a selected cell population, where these forms may have the desirable property of high stability in human serum. This new prodrug activation strategy is based on the remarkable and unexpected self-elimination reaction of aminobenzyl ethers as illustrated in Scheme 1.

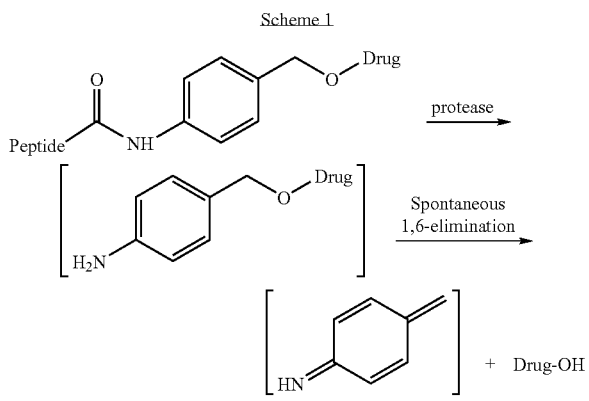

The drug conjugates of this invention comprise at least one drug moiety, and a prodrug linker. The prodrug linker is made up of an aminobenzyl ether-based self-immolative spacer, a peptide comprising a recognition/cleavage site for the enzymes, and optional moieties such as one or more of an acyl unit, and a second self-immolative spacer which separates the drug and the aminobenzyl ether spacer. In one aspect, the prodrug linker joins (links, couples) the drug residue to a ligand for a biological receptor. In another aspect, the prodrug linker has an N-terminus in addition to the terminus that is coupled to the drug residue, where the N-terminus is blocked by a protecting group. In one aspect, the drug conjugates may be represented by the general formulas (I) and (II)

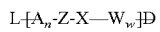
(I)

wherein: D is a drug residue; L is a ligand; A is an optional acyl unit; Z is a peptide comprising one or more amino acids; X is an aminobenzyl ether self-immolative group; W is an optional (second) self-immolative group; n is an integer of 0 or 1; and w is an integer of 0 or 1, where, $-[A_n\text{-}Z\text{-}X-W_w-]$ represents a group referred to herein as a prodrug linker.

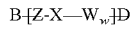
(II)

wherein: D is a drug residue; B is a blocking group; Z is a peptide comprising one or more amino acids; X is an aminobenzyl ether self-immolative group; W is an optional second self-immolative group; and w is an integer of 0 or 1, where $-[Z\text{-}X-W_w-]$ represents a group referred to herein as the prodrug linker.

In a preferred aspect, the present invention provides a compound of the formula

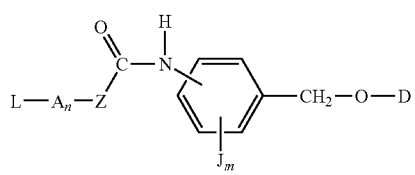

wherein: —O-D is a portion of a drug, where the drug has the formula HO-D, where in a preferred embodiment the HO— is joined to an aromatic ring of the drug residue D; J is an optional substituent, which is selected independently at each occurrence, and may occur as many as four times on the aromatic ring shown in the formula, and m is 0, 1, 2; 3 or 4;

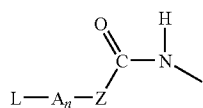

is situated at an ortho- or para-position with respect to the —CH$_2$— group; Z is a peptide comprising one or more amino acids; A is an acyl unit where n is 0 or 1; and L is a ligand.

In another preferred aspect, the present invention provides a compound of the formula

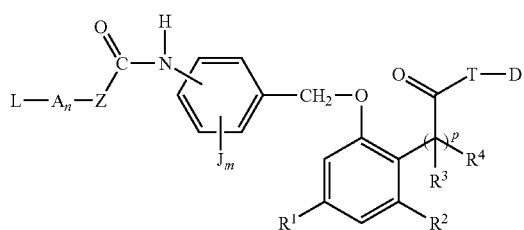

wherein: -T-D is a portion of a drug, where the drug has the formula HT-D; T is O, S, NH, or N(lower alkyl, i.e., C$_{1-6}$alkyl); J is a substituent group, and m is 0, 1, 2; 3 or 4;

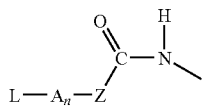

is situated at an ortho- or para-position with respect to the —CH$_2$— group; Z is a peptide comprising one or more amino acids; A is an acyl unit and n is 0 or 1; L is a ligand; p is 1 or 2; and each of R$^1$, R$^2$, R$^3$ and R$^4$ is independently selected from H and C$_1$-C$_5$ alkyl.

In another preferred aspect, the present invention provides a compound of the formula

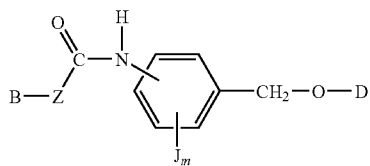

wherein: —O-D is a portion of a drug, where the drug has the formula HO-D, and in a preferred embodiment the HO— is joined to an aromatic ring of D; J is a substituent group, and m is 0, 1, 2; 3 or 4;

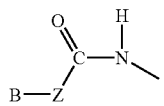

is situated at an ortho- or para-position with respect to the —CH$_2$— group; Z is peptide comprising one or more amino acids; and B is hydrogen or a blocking group selected from a D-amino acid and an N-terminus protecting group.

In another preferred aspect, the invention provides a compound of the formula

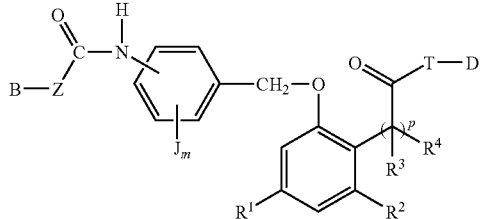

wherein: -T-D is a portion of a drug, where the drug has the formula HT-D; T is O, S, NH, or N(lower alkyl); J is a substituent group, and m is 0, 1, 2; 3 or 4;

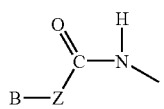

is situated at an ortho- or para-position with respect to the —CH$_2$— group; Z is an amino acid or a peptide; p is 1 or 2;

and B is hydrogen or a blocking group selected from a D-amino acid and an N-terminus protecting group.

The above and other aspects of the present invention are achieved through derivatizing a drug by attaching it to a prodrug linker via a reactive functional group of the drug. In one aspect, the drug may be derivatized through a reactive functional group that is important for the biological activity of the drug thereby inhibiting or reducing the pharmacological activity of the drug to thereby convert the drug into a pharmacologically inactive or relatively inactive peptidyl derivative conjugate. The prodrug linker contains a peptide specifically tailored so as to render a drug conjugate of the present invention a selective substrate susceptible to enzymatic cleavage by one or more proteases, e.g., preferably lysosomal proteases, such as cathepsin B, C or D. The enzymatic cleavage reaction will remove the prodrug linker from the drug moiety by triggering the self-elimination of the aminobenzyl ether spacer group, and affect the release of the drug in its pharmacologically active form.

In one aspect, the present invention provides drug conjugates having superior serum stability. For example, in contrast to drug conjugates wherein a hydroxyl group of a drug is linked to a spacer via a labile carbonate linkage that is susceptible to rapid hydrolysis in aqueous buffer or human serum, the drug conjugates of the present invention utilizing a benzyl ether linkage are relatively more stable under the same conditions, and selectively undergo ether fragmentation to release the drug upon treatment with protease, e.g., cathepsin B. Serum stability is a desirable property for drug conjugates where it is desired to administer inactive drug to the patient's serum, have that inactive drug concentrate at a target by way of the ligand, and then have that drug conjugate converted to an active form only in the vicinity of the target.

In one aspect, the present invention provides drug conjugates that are characterized by the capability of the drug conjugate to target a selected cell population, for example, a tumor site. In one aspect, the drug conjugate comprises a ligand that is linked to a drug moiety through a prodrug linker. The ligand serves to deliver the drug conjugate to the desired target site by binding to a receptor distinctively associated with the cell population at the target site. In another aspect, the peptide of a ligand-free drug conjugate is a highly selective substrate for tumor specific enzymes that are present at the tumor site in sufficient amounts to generate cytotoxic levels of free drug in the proximity of the tumor.

Ideally, the toxic activity of the drug is greatly reduced or absent when the drug is bonded directly to the prodrug linker where the prodrug linker is further coupled with either a ligand or a blocking group. Because the free drug is only released in the proximity of a targeted cell population, the conjugates of the present invention provide both specificity and therapeutic drug activity for the treatment of the selected cell population. They may be used in a pharmaceutical composition, such as one comprising a pharmaceutically effective amount of a compound of Formula I or II below, in admixture with a pharmaceutically acceptable carrier, diluent or excipient.

In another aspect, the invention provides methods for treatment of cancers or precancerous conditions and other tumors in animal subjects. For instance, the invention provides compounds and compositions for use in a method for treating tumors wherein the animal subject is treated, in a pharmaceutically acceptable manner, with a pharmaceutically effective amount of a compound or composition of the present invention. Representative examples of precancerous conditions, include, but are not limited to, metaplasia, hyperplasia, dysplasia, colorectal polyps, actinic ketatosis, actinic cheilitis, human papillomaviruses, leukoplakia, lychen planus and Bowen's disease.

In another aspect, the present invention provides compositions comprising an effective amount of a drug conjugate and a pharmaceutically acceptable carrier or vehicle.

In another aspect, the present invention provides methods for killing or inhibiting the multiplication of a tumor cell or cancer cell, comprising administering to an animal in need thereof an effective amount of a drug conjugate.

In yet another aspect, the invention provides methods for treating cancer, comprising administering to an animal in need thereof an effective amount of a drug conjugate.

In another aspect, the invention provides methods for killing or inhibiting the replication of a cell that expresses an auto-immune antibody, comprising administering to an animal in need thereof an effective amount of a drug conjugate.

In yet another aspect, the invention provides methods for treating an autoimmune disease, comprising administering to an animal in need thereof an effective amount of a drug conjugate.

In still another aspect, the invention provides methods for treating an infectious disease, comprising administering to an animal in need thereof an effective amount of a drug conjugate.

In another aspect, the present invention provides methods for preventing the multiplication of a tumor cell or cancer cell, comprising administering to an animal in need thereof an effective amount of a drug conjugate.

In yet another aspect, the invention provides methods for preventing cancer, comprising administering to an animal in need thereof an effective amount of a drug conjugate.

In another aspect, the invention provides methods for preventing the multiplication of a cell that expresses an auto-immune antibody, comprising administering to an animal in need thereof an effective amount of a drug conjugate.

In yet another aspect, the invention provides methods for preventing an autoimmune disease, comprising administering to an animal in need thereof an effective amount of a drug conjugate.

In still another aspect, the invention provides methods for preventing an infectious disease, comprising administering to an animal in need thereof an effective amount of a drug conjugate.

The present invention may be understood more fully by reference to the following detailed description, Figures and illustrative examples, which are intended to exemplify non-limiting embodiments of the invention.

4. BRIEF DESCRIPTION OF THE DRAWINGS

5. DETAILED DESCRIPTION OF THE INVENTION

Figure 1:
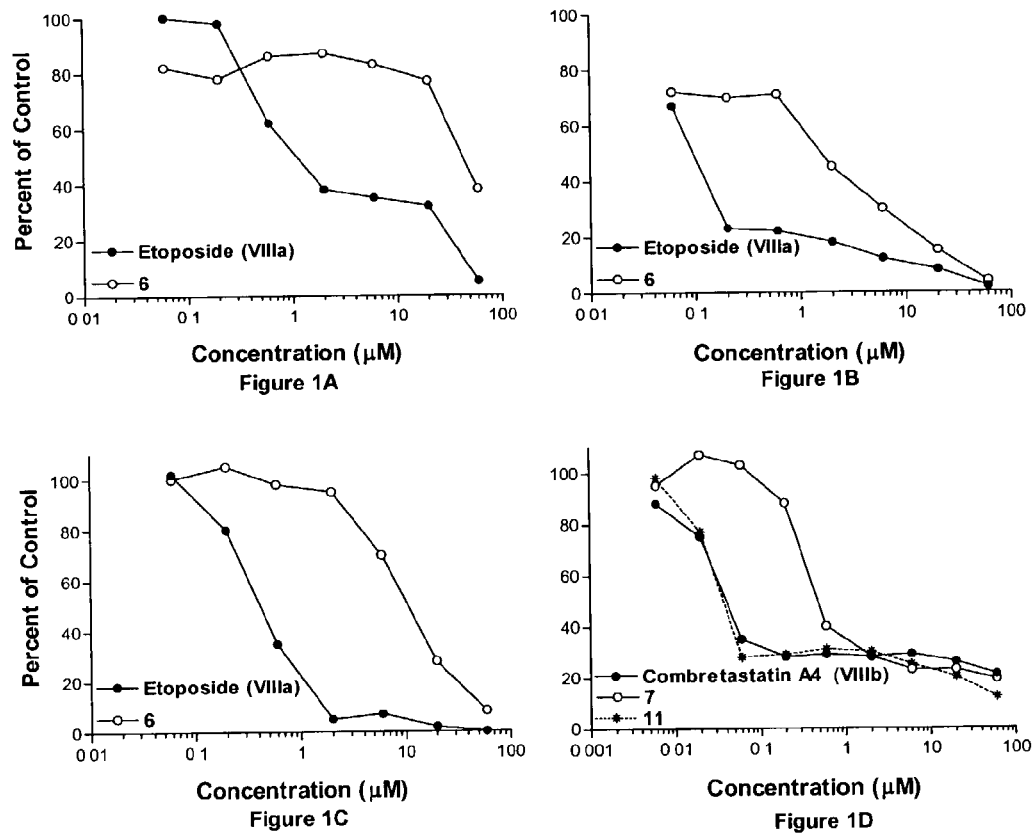
FIG. 1 is a graph showing the cytotoxic effects on L2987 human lung adenocarcinoma (A and D), WM266/4 (B), and IGR-39 (C) human melanoma cell lines. The cells were exposed to various concentrations of the drugs for 24 h, washed, incubated for a further 48 h, and the cytotoxic activities were quantified through the incorporation of [$^3$H] thymidine relative to untreated control cells.
Figure 2A:
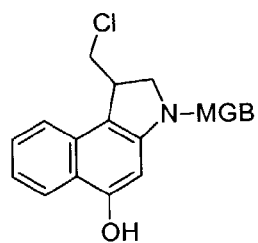
FIGS. 2A, 2B, 2C, 2D and 2E illustrate the chemical structures of exemplary drugs that may be incorporated into prodrugs of the present invention.
Figure 2A:
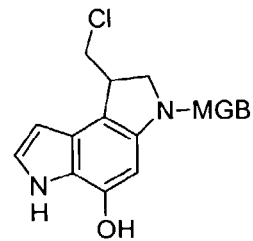
Figure 2A:
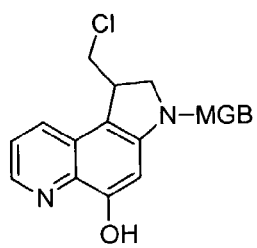
Figure 2A:
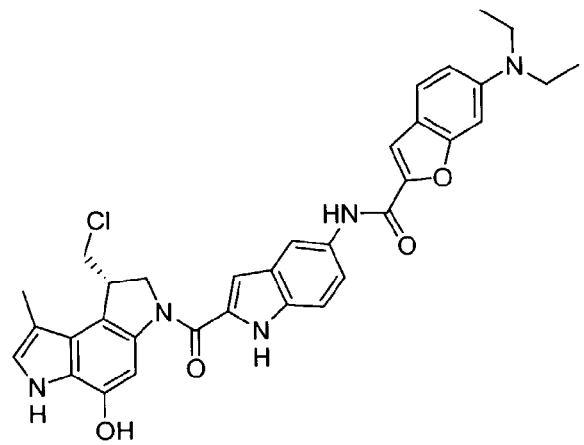
Figure 2B:
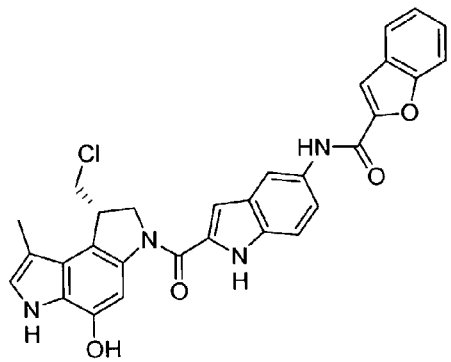
Figure 2B:
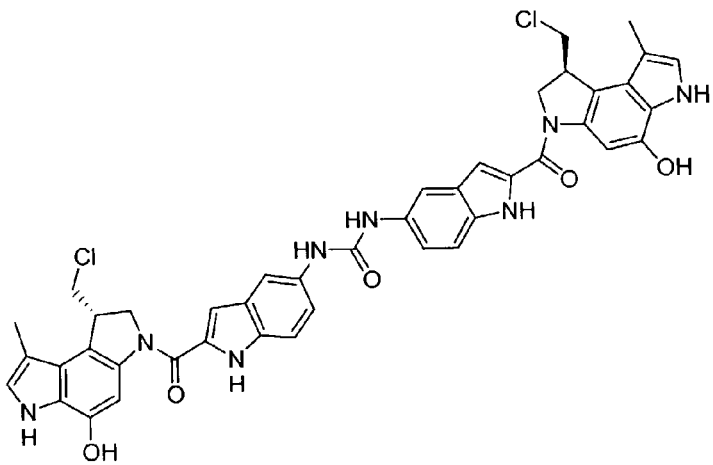
Figure 2B:
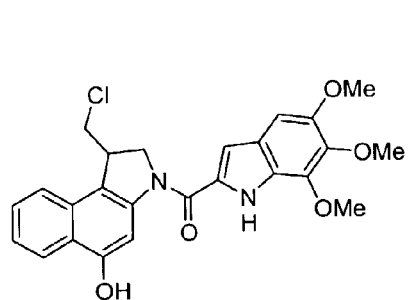
Figure 2B:
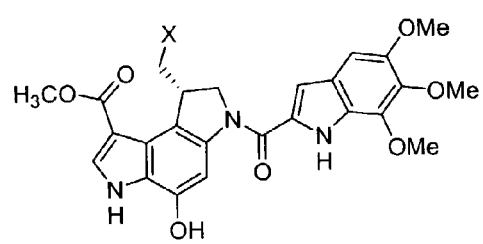
Figure 2C:
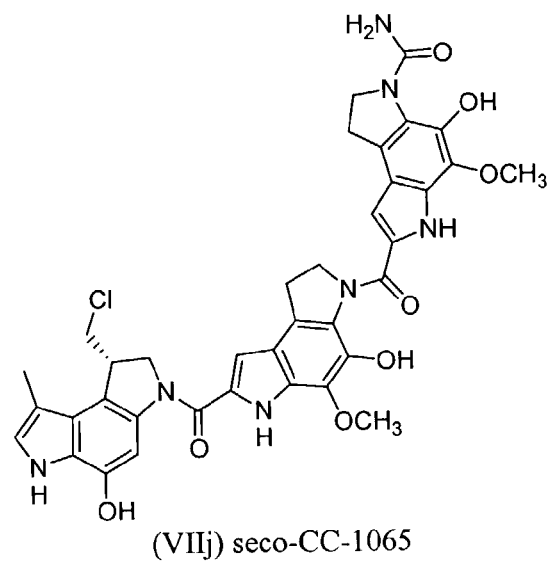
Figure 2C:
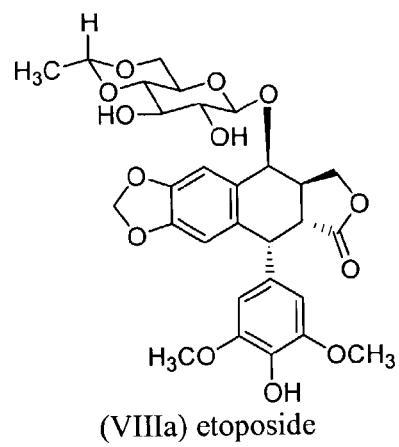
Figure 2C:
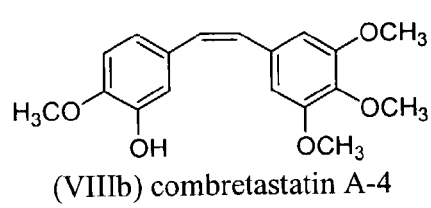
Figure 2C:
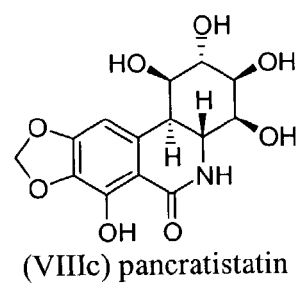
Figure 2D:
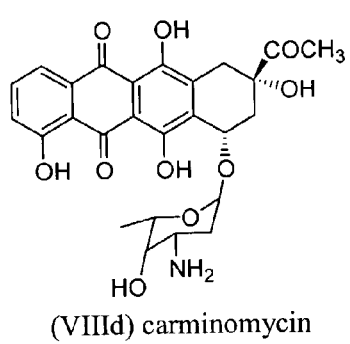
Figure 2D:
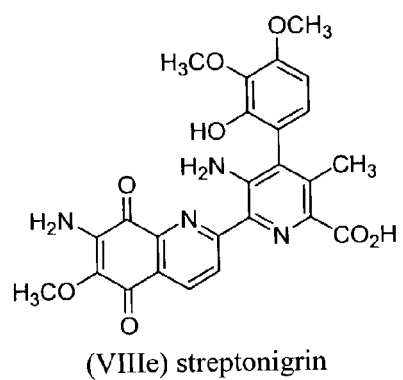
Figure 2D:
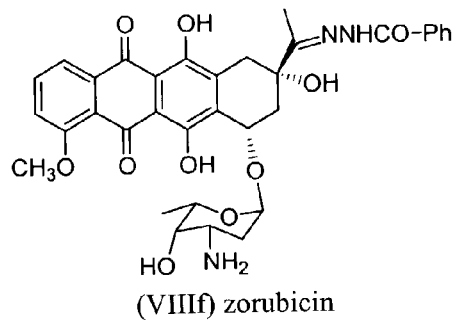
Figure 2D:
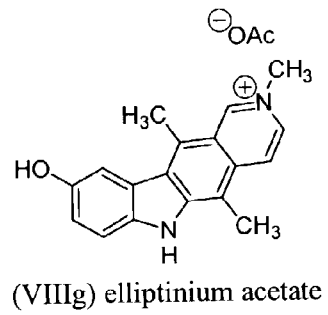
Figure 2E:
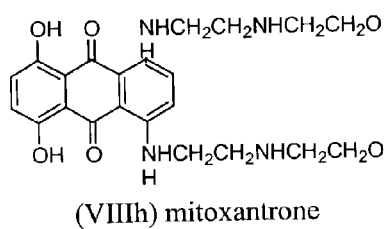
Figure 2E:
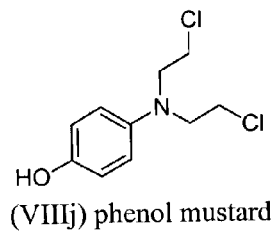
Figure 2E:
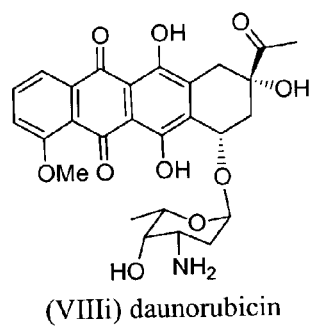
Figure 2E:
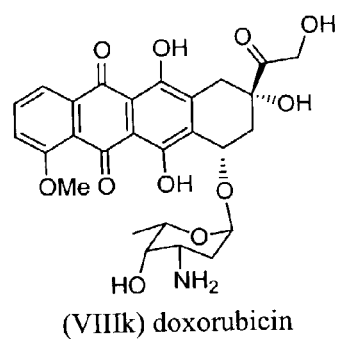
Figure 2E:
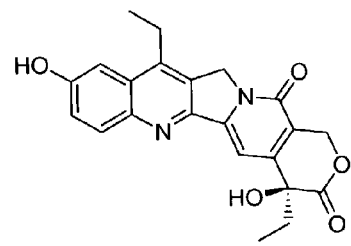

In one aspect, the present invention provides novel drug conjugates comprised of a ligand capable of targeting a selected cell population, and a drug connected to the ligand via a prodrug linker. The peptide-containing prodrug linker, shown as the group of chemical moieties within the square brackets in (I), is composed of an amino acid or a peptide (Z), an aminobenzyl ether self-immolative spacer (X), an optional acyl unit (A$_n$), and an optional second self-immolative spacer (W), which may separate the drug from the aminobenzyl ether group. Thus, the invention provides a conjugate represented by general formula (I):

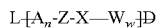  (I)

wherein: D is a drug moiety; L is a ligand; A is an optional acyl unit; Z is an amino acid or a peptide; X is an aminobenzyl ether self-immolative group; W is an optional second self-immolative group; n is an integer of 0 or 1; and w is an integer of 0 or 1, where, -[A$_n$-Z-X—W$_w$-] represents a group referred to herein as a prodrug linker.

Another aspect of the invention provides drug conjugates wherein a blocking group is situated in the place of the ligand to protect the N-terminus of the peptide. Such drug conjugates may be selectively activated by enzymes naturally enriched in association with a selected cell population. Thus, the invention provides a conjugate represented by the general formula (II):

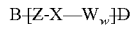  (II)

wherein: D is a drug moiety; B is a blocking group; Z is an amino acid or a peptide; X is an aminobenzyl ether self-immolative group; W is an optional second self-immolative group; and w is an integer of 0 or 1, where -[Z-X—W$_w$-] represents a group referred to herein as a prodrug linker.

In another aspect, the present invention provides a compound of the formula

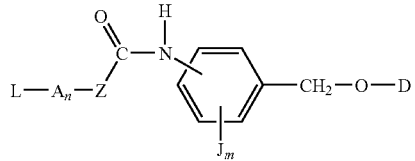

wherein: —O-D is a portion of a drug, where the drug has the formula HO-D and in a preferred embodiment the HO— is joined to an aromatic ring of D; J is a substituent group, and m is 0, 1, 2; 3 or 4;

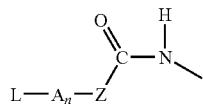

is situated at an ortho- or para-position with respect to the —CH$_2$— group; Z is an amino acid or a peptide; A is an acyl unit where n is 0 or 1; and L is a ligand.

In another aspect, the present invention provides a compound of the formula

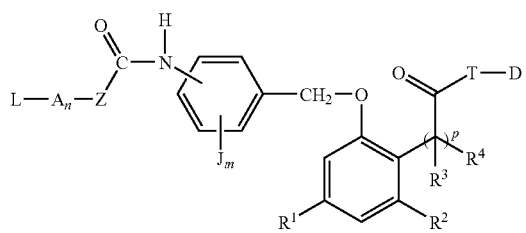

wherein: D is a drug comprising a T moiety; T is O, S, NH, or N(lower alkyl); J is a substituent group, and m is 0, 1, 2; 3 or 4;

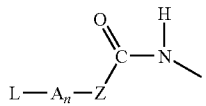

is situated at an ortho- or para-position with respect to the —CH$_2$— group; Z is an amino acid or a peptide; A is an acyl unit and n is 0 or 1; L is a ligand; p is 1 or 2; and each of R$^1$, R$^2$, R$^3$ and R$^4$ is independently selected from H and C$_1$-C$_5$ alkyl.

In another aspect, the present invention provides a compound of the formula

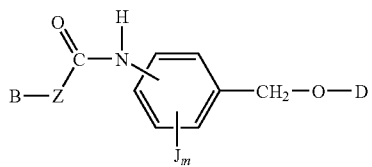

wherein: —O-D is a portion of a drug, where the drug has the formula HO-D and in a preferred embodiment the HO— is joined to an aromatic ring of D; J is a substituent group, and m is 0, 1, 2; 3 or 4;

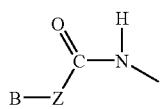

is situated at an ortho- or para-position with respect to the —CH$_2$— group; Z is an amino acid or a peptide; and B is hydrogen or a blocking group selected from a D-amino acid and an N-terminus protecting group.

In another aspect, the invention provides a compound of the formula

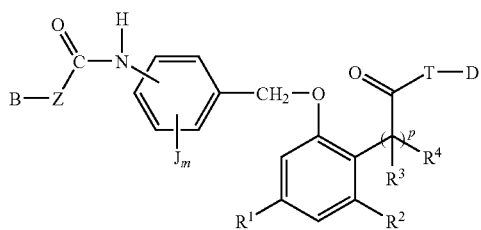

wherein: D is a drug comprising a T moiety; T is O, S, NH, or N(lower alkyl); J is a substituent group, and m is 0, 1, 2; 3 or 4;

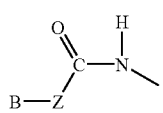

is situated at an ortho- or para-position with respect to the —CH$_2$— group; Z is an amino acid or a peptide; p is 1 or 2; and B is hydrogen or a blocking group selected from a D-amino acid and an N-terminus protecting group.

Before describing the present invention in further detail, the following terms as used herein are given the indicated meaning.

The term "prodrug" and the term "drug conjugate" are used herein interchangeably. Both refer to a compound that is relatively innocuous to cells while still in the conjugated form but which is selectively degraded to a pharmacologically active form by conditions, e.g., enzymes, located within or in the proximity of target cells.

The term "selective" as used in connection with enzymatic cleavage means a greater rate of cleavage of a peptidyl component of the instant invention relative to cleavage of a peptide which comprises a random sequence of amino acids. Therefore, the peptidyl component of the instant invention is a preferred substrate of the enzymes associated with the targeted cell population. The term "selective" also indicates that the peptide is cleaved at the site where it is coupled to the amino group of the aminobenzyl ether spacer.

The term "cytotoxic" means arresting the growth of, or killing, cells.

The term "hydroxylic drug" means a drug containing a hydroxyl group through which the drug may be coupled to the prodrug linker.

The term "amino acid" as used herein, refers to both naturally occurring amino acids and unnatural amino acids.

The term "D-amino acid" as used herein, refers to an amino acid having a D-configuration. A D-amino acid may be a naturally occurring amino acid or an unnatural amino acid.

The term "aromatic" means a cyclic conjugated compound with all or some of the atoms in the ring being carbons.

The term "minor groove binder" is a molecule that binds to and/or within the minor groove of double stranded deoxyribonucleic acid (DNA).

The term "ligand" means any molecule that specifically binds or reactively associates or complexes with a receptor, substrate, antigenic determinant, or other binding site on a target cell or tissue. Examples of ligands include antibodies (e.g., a monoclonal antibody), enzymes (e.g., fibrinolytic enzymes), biologic response modifiers (e.g., interleukins, interferons, erythropoeitin, or colony stimulating factors), peptide hormones, and antigen-binding fragments thereof. The ligand can be linked directly, or through an acyl unit, to the peptide.

As used herein, "immunoglobulin" may refer to any recognized class or subclass of immunoglobulins such as IgG, IgA, IgM, IgD, or IgE. The immunoglobulin can be derived from any species.

The term "antibody," as used herein, refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce auto-immune antibodies associated with an autoimmune disease. The immunoglobulin disclosed herein can be of any type (e.g., IgG, IgE, IgM, IgD, IgA and IgY), class (e.g., $IgG_1$, IgG2, IgG3, IgG4, IgA1 and IgA2) or subclass of immunoglobulin molecule. The immunoglobulins can be derived from any species. Preferably, however, the immunoglobulin is of human, murine, or rabbit origin. Antibodies useful in the invention are preferably monoclonal, and include, but are not limited to, polyclonal, monoclonal, bispecific, human, humanized or chimeric antibodies, single chain antibodies, Fv, Fab fragments, F(ab') fragments, F(ab')2 fragments, fragments produced by a Fab expression library, anti-idiotypic (anti-Id) antibodies, CDR's, and epitope-binding fragments of any of the above which immunospecifically bind to cancer cell antigens, viral antigens or microbial antigens.

The term "blocking group" refers to an atom or a chemical moiety that protects the N-terminus of an amino acid or a peptide from undesired reactions via this reactive site. A blocking group used during the synthesis of a drug conjugate of the invention should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry Exemplary blocking groups include, but are not limited to, hydrogen, D-amino acid, and carbobenzoxy (Cbz) chloride.

The term "peptide linker" in the present invention refers to the peptide moiety that links the drug moiety to the ligand in (I) or the blocking group in (II). The peptide linker is made up of an aminobenzyl ether self-immolative spacer, an amino acid or peptide, an optional acyl unit, and an optional second self-immolative spacer.

The term "self-immolative spacer" refers to a bifunctional chemical moiety which is capable of covalently linking together two spaced chemical moieties into a normally stable tripartate molecule. It will spontaneously separate from the second moiety if its bond to the first moiety is cleaved.

The terms "peptide" and "peptidic" refer to a single amino acid or a plurality of amino acids that are joined together by amide bonds.

The term "acyl" refers to an organic radical derived from a carboxylic acid by the removal of the hydroxyl group.

The term "acyl unit" means a bifunctional agent containing two distinctly reactive sites, one of which is a carboxylic acid or a reactive equivalent thereof. The carboxylic acid or reactive equivalent is joined to the N-terminus of the amino acid or a peptide through an amide linkage. The other reactive site of the acyl unit is coupled to the ligand of interest, such as an antibody. Examples of such "other" reactive sites include maleimides and haloacetamides that react with thiol groups on a ligand, e.g., mAbs; thiols that react with disulfides on a ligand, e.g., mAbs; active disulfides that react with thiols on a ligand; hydrazides that react with aldehydes and ketones on a ligand, e.g., mAbs, and hydroxysuccinimides, isocyanates, isothiocyanates, and anhydrides that react with amino groups on a ligand, e.g., mAbs.

In various aspects, the present invention provides: drug conjugates which are selectively activatable at the site of the tumor; tumor specific drug conjugates where the tumor specificity arises solely from the ligand; drug conjugates that are highly selective substrates for tumor specific enzymes, where these enzymes are present in the proximity of the tumor in sufficient amounts to generate cytotoxic levels of free drug in the vicinity of the tumor, and the ligand may optionally be omitted so that the N-terminus of the peptide is instead blocked using a conventional protecting group; tumor-specific drug conjugates that are stable to adventitious proteases in the human serum; tumor-specific drug conjugates in accordance with the preceding aspects, which are less toxic than the corresponding free drug; method for the production of drug conjugates and pharmaceutical compositions and methods for delivering the conjugates to target cells in which a modification in biological process is desired, such as in the treatment of diseases such as cancer; and a method for delivering to the site of tumor cells in a warm-blooded animal an active antitumor drug by administering to said warm-blooded animal the drug-ligand conjugate according to this invention.

In various preferred embodiments of the invention: the drug contains a reactive hydroxyl group, having a pKa of 16 or less; the drug contains a hydroxyl group joined to an aromatic moiety of the drug and this hydroxyl group is used to conjugate the drug to the remainder of the drug conjugate; the drug is 1,2,9,9a-tetra-hydro-cyclo-propa[c]benz[e]indol-4-one (CBI) conjugated to a minor groove binder (MGB); the peptide is valine-citrulline, the blocking group is carbobenzoxy (Cbz), and w is 0; the drug moiety is cyclopropapyrroloindole (CPI) conjugated to a minor groove binder, the peptide is valine-citrulline, the blocking group is carbobenzoxy (Cbz), and w is 0; the drug moiety is 1,2,9,9a-tetra-hydro-cyclo-propa[c]pyrido[3,2-e]indol-4-one (CPyI) conjugated to a minor groove binder (MGB), the peptide is valine-citrulline, the blocking group is carbobenzoxy (Cbz), and w is 0; the drug moiety is combretastatin A-4, the blocking group is carbobenzoxy (Cbz), the peptide is phenylalanine-lysine, the blocking group is carbobenzoxy (Cbz), and w is 0; the drug moiety is 1,2,9,9a-tetra-hydro-cyclo-propa[c]benz[e]indol-4-one (CBI) conjugated to a minor groove binder (MGB), the peptide is phenylalanine-lysine, the blocking group is carbobenzoxy (Cbz), and w is 0; the drug moiety is cyclopropa-pyrroloindole (CPI) conjugated to a minor groove binder, the peptide is phenylalanine-lysine, the blocking group is carbobenzoxy (Cbz), and w is 0; the drug moiety is 1,2,9,9a-tetra-hydro-cyclo-propa[c]pyrido[3,2-e]indol-4-one (CPyI) conjugated to a minor groove binder (MGB), the peptide is phenylalanine-lysine, the blocking group is carbobenzoxy (Cbz), and w is 0; the drug moiety is an anthracycline antibiotic, the ligand is an antibody, A is an acyl unit, the peptide is valine-citrulline, and w is 1; the drug moiety is taxol, the ligand is an antibody, A is an acyl unit, the peptide is valine-citrulline, and w is 1; the drug moiety is a mitomycin C, the ligand is an antibody, A is an acyl unit, the peptide is valine-citrulline, and w is 1; the drug moiety is an anthracycline antibiotic, the ligand is an antibody, A is an acyl unit, the peptide is phenylalanine-lysine, and w is 1; the drug moiety is taxol, the ligand is an antibody, A is an acyl unit, the peptide is phenylalanine-lysine, and w is 1; and the drug moiety is a mitomycin C, the ligand is an antibody, A is an acyl unit, the peptide is phenylalanine-lysine, and w is 1.

For a better understanding of the invention, the components of the inventive drug conjugates, i.e., the drugs, ligands, blocking groups, peptides and self-immolative groups, will be discussed individually below. The synthesis of the conjugates will then be described.

5.1. The Prodrug Linker

The prodrug linker of the present invention covalently links the drug moiety to the ligand/blocking group in forming the drug conjugate of the present invention. The linker comprises a peptide, a self-immolative aminobenzyl ether spacer and an optional acyl unit. It may also contain a second self-immolative spacer (W). Each of these components will now be described.

5.1.1. Self-Immolative Spacer

A drug conjugate in accordance with the present invention employs an aminobenzyl ether group,

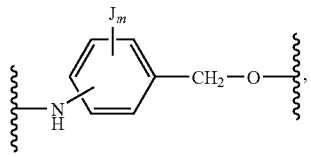

that functions as a self-immolative spacer. This group is denoted by the symbol "X" in the structures shown herein, e.g., in formulas I and II. In a preferred aspect, the aminobenzyl ether group covalently links a drug residue (via the ether group) to a peptide (via the amino group) to provide a tripartate molecule. This tripartate molecule is preferably stable and pharmacologically inactive in the absence of the target enzyme. However, upon action of the target enzyme, or any other suitable cleavage conditions, the bond indicated by the arrow in the figure below will be cleaved.

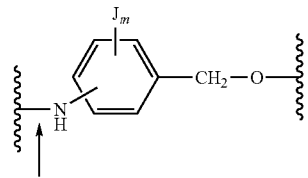

In one aspect, the amino group shown in the figure above is bonded to a carbonyl group. In another aspect, the amino group shown in the figure above in combination with the carbonyl group forms part of a peptidic linkage which is susceptible to enzyme-catalyzed cleavage. Upon such cleavage, whether by enzymatic or other means, e.g., hydrolysis means, the aminobenzyl ether group undergoes a spontaneous reaction that causes cleavage of the bond shown by the arrow in the figure

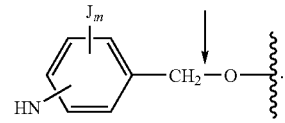

This cleavage leaves the oxygen of the ether group attached to the drug residue, thereby allowing reformation of the drug at the site of cleavage.

The line from the amine functionality of X into the ring of X indicates that the amine functionality may be bonded to any of the five carbons that both form the ring and are not substituted with the —CH$_2$—O— group that is necessarily bonded to the ring. Preferably, the amine functionality of X is covalently bound to the aromatic ring of the benzylether group at either the para, or at an ortho position on the ring, relative to the —CH$_2$O— group. Thus, in preferred aspects, X may be represented by formulas (III) and (IV).

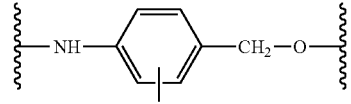 (III)

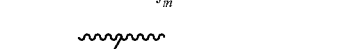 (IV)

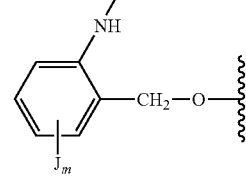

In one aspect, the X group is represented by formula (III), in another aspect the X group is represented by formula (IV), and in yet another aspect the X group is selected from formulas (III) and (IV).

The aromatic ring of the aminobenzyl ether group may optionally be substituted with one or more "J" groups. A "J" group is a substituent on the aromatic ring, which replaces a hydrogen that is otherwise attached to one of the four nonsubstituted carbons that form the ring. The J group, which may be a single atom, e.g., a halogen, or a multi-atom group, e.g., methyl, is selected in order to impact the stability of the aminobenzyl ether or the decomposition product thereof. Electron withdrawal from the ring may be used to facilitate the spontaneous decomposition of the aminobenzyl group from the drug after cleavage of the bond between the amino group of the aminobenzyl ether group and the adjacent peptide linkage. Exemplary J substituents include F, Cl, Br, $NO_2$, $NHCOCH_3$, $N(CH_3)_2$, $NHCOCF_3$, alkyl, and haloalkyl, where m is an integer of 0, 1, 2, 3 and 4.

A preferred self-immolative spacer suitable for use in the present invention is para-aminobenzyl ether wherein m is 0. Another preferred spacer suitable for use in the present invention incorporates an electron deficient group such as $NO_2$ at the meta position with respect to the benzyl ether. In one aspect, one nitro group is attached to the aromatic ring of the benzyl ether group.

When the drug has a hydroxyl group that may be used to link the drug to the remainder of the prodrug, then the aminobenzyl ether group may be linked directly to the drug residue. However, if the drug does not contain a hydroxyl group, but instead contains some other reactive functional group that may serve to link the drug to a self-immolative spacer, then such drugs may still be incorporated into an aminobenzyl ether-containing prodrug of the present invention by including a second, intermediate self-immolative spacer between the drug residue and the aminobenzyl ether group. The intermediate self-immolative spacer is denoted herein by the symbol "W".

In one aspect, the second spacer moiety W is represented by the formula (V)

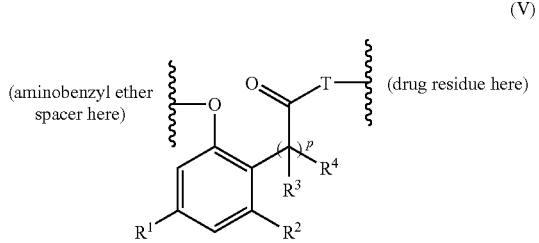

(V)

wherein, T is O, NH, N(lower alkyl) or S, p is 1 or 2, and each of $R^1$, $R^2$, $R^3$ and $R^4$ is independently selected from H and $C_1$-$C_5$ alkyl. The lower alkyl group has 1, 2, 3, 4, 5 or 6 carbons, i.e., is a $C_{1-6}$alkyl group. Such spacer groups are described in, for example, U.S. Pat. No. 6,210,345, where is incorporated herein by reference in its entirety for all purposes. The chemistry described in U.S. Pat. No. 6,210,345 to incorporate the group W into a drug conjugate may be employed to add an aminobenzyl ether to a drug conjugate according to the present invention.

5.1.2. Peptide

In the conjugate of Formulas I and II, the peptide Z is the amidification residue of a single amino acid or a plurality of amino acids that are joined together by amide bonds. The peptide in a compound of the invention is selected with the goal of directing enzyme-catalyzed cleavage of an amide group that is joined to the amino group of the aminobenzyl ether spacer. The peptide may also be selected to be particularly responsive to an enzyme that is in a location of interest in a biological system. The peptide typically comprises 2-4 amino acid residues, however, more than 4 amino acid residues may be present in the peptide, e.g., 6 or 8. Peptide sequences that are susceptible to cleavage by specific enzymes or classes of enzymes are well known in the art.

The N-terminus of the peptide linker may be directly linked to a carboxyl functionality of a ligand, or may be indirectly bonded to a ligand via an acyl unit, as describe below.

The following group of exemplary peptide groups, are named in order to illustrate further the conjugates of the present invention: Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly [SEQ ID NO: 1], Ala-Leu-Ala-Leu [SEQ ID NO:2], Phe-$N^9$-tosyl-Arg, Phe-$N^9$-nitro-Arg. Some preferred peptides include one or any combination of Phe-Lys, Val-Lys, Val-Cit, and D-Phe-L-Phe-Lys.

Numerous specific peptide linker molecules suitable for use in the present invention can be designed and optimized for their selectivity for enzymatic cleavage by a particular tumor-associated protease. The preferred peptide linkers for use in the present invention are those that are optimized toward the proteases, such as cathepsin B. As described in further detail below, cathepsin B was shown to rapidly release the drug etoposide from a drug conjugate of the present invention at pH 5.1 at 37° C. (160 mmol/min/mg Cathepsin B), but in the absence of the added enzyme there was no breakdown of the conjugate after a week at pH 5.1 at 37° C.

5.1.3. Acyl Unit

In the conjugates of Formula I, A is an optional acyl unit that joins Z to the ligand. The peptide group Z will typically terminate in an amino group. If the ligand has an amino-reactive group that may be used to incorporate the ligand into the prodrug, then the acyl unit is not necessary; although it may still be employed. However, if the ligand does not have an amino-reactive group, or does not contain an amino-reactive group that is desirably used to incorporate the ligand into the prodrug, then an acyl unit is conveniently included in a prodrug of the invention. The acyl unit contains an acyl group that may be reacted with the amino-terminus of the peptide linkage Z, and also contains a second reactive group that is reactive with a functional group on the ligand that is desirably used to incorporate the ligand into the prodrug. In other words, an acyl unit is defined as a bifunctional agent containing separate reactive sites, the first of which is a carboxylic acid or a reactive equivalent thereof. This first reactive site may be joined to the N terminus of an amino acid or a peptide through an amide linkage. The second reactive site is used to couple to the ligand of interest, such as antibodies.

Suitable bifunctional reactive linker groups are well known in the art, see S. S. Wong, Chemistry of Protein Conjugation and Cross-Linking, CRC Press, Inc., Boston, 1991. Exemplary second reactive sites are selected from maleimides and haloacetamides that may be used to react with thiol groups on a ligand, e.g., mAbs; thiols that react with disulfides on a ligand, e.g., mAbs; active disulfides that react with thiols on the ligand, e.g., mAb thiols; hydrazides that react with aldehydes and ketones on the ligand, e.g., mAbs, and hydroxysuccinimides, isocyanates, isothiocyanates, and anhydrides that react with amino groups on the ligand, e.g., mAbs.

A preferred acyl unit is the compound of formula (VI).

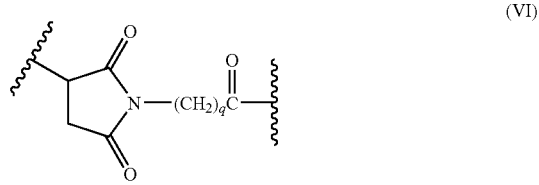

wherein q is 1-10, or 3-6, or 5.

5.2 The Drug

As used herein, the terms "drug" or "D" refer to any compound possessing a desired biological activity and a reactive functional group that may be used to incorporate the drug into the conjugate of the invention. The desired biological activity includes the diagnosis, cure, mitigation, treatment, or prevention of disease in man or other animals. Thus, so long as it has the needed reactive functional group, the term "drug" refers to chemicals recognized as drugs in the official United States Pharmacopeia, official Homeopathic Pharmacopeia of the United States, or official National Formulary, or any supplement thereof Exemplary drugs are set forth in the Physician's Desk Reference (PDR) and in the Orange Book maintained by the U.S. Food and Drug Administration (FDA). New drugs are being continually being discovered and developed, and the present invention provides that these new drugs may also be incorporated into a prodrug form of the present invention. Exemplary drugs are shown in FIGS. 2A-2E.

In various aspects of the invention the drug is: a cytotoxic drug useful in cancer therapy; a protein or polypeptide possessing a desired biological activity, such as a toxin, e.g., abrin, ricin A, pseudomonas exotoxin, and diphtheria toxin; other suitable proteins include tumor necrosis factor, α-interferon, β-interferon, nerve growth factor, platelet derived growth factor, and tissue plasminogen activator; and biological response modifiers such as, for example, lymphokines, interleukin-1 ("IL-1"), interleukin-2 ("IL-2"), interleukin6 ("IL-6"), granulocyte macrophage colony stimulating factor ("GM-CSF"), granulocyte colony stimulating factor ("G-CSF"), or other growth factors.

The term "derivatives thereof" as used herein includes any naturally occurring derivatives and synthetically prepared analogs of a drug. Representative examples of derivatives of drugs disclosed herein include, but are not limited to camptothecin derivatives, such as topotecan, CPT-11 and 9-AC; taxol derivatives, such as taxotere; and the etoposide (VP-16) derivative, teniposide.

The drug conjugates as represented by formula I of the present invention are effective for the usual purposes for which the corresponding drugs are effective, and have superior efficacy because of the ability, inherent in the ligand, to transport the drug to the desired cells where it is of particular benefit.

The drug conjugates as represented by formula II of the present invention are effective for the usual purposes for which the corresponding drugs are effective, and have superior efficacy because they are capable of being selectively activated by enzymes associated with the cell population of interest.

In the drug conjugates of formulas I and II, when the only spacer is an aminobenzyl ether group (w=0), D is a drug that contains a hydroxyl group by means of which the drug is coupled to the aminobenzyl ether spacer group. Upon enzyme-activated fragmentation, as shown in Scheme 1, the aminobenzyl ether group decomposes to form an iminoquinone methide compound and the drug. It is speculated that initially upon decomposition, the drug is present in the form of an anion, i.e., a compound of the formula D-O⁻, which is the conjugate base of a drug with the formula D-OH. Accordingly, as one factor in understanding the kinetics of the decomposition process, the stability of the D-O⁻ structure may be considered important. Thus, in a preferred embodiment, the drug has a hydroxyl group that is relatively acidic, i.e., has a relatively stable conjugate base of the formula D-O⁻. In various aspects of the invention, the pKa of the "linking" hydroxyl group of the drug is 16 or less, 15 or less, 14 or less, 13 or less, 12 or less, 11 or less, 10 or less, 9 or less, and typically, the pKa will be greater than 3, or greater 4, or greater than 5, where the invention includes each possible combination of the listed lower and upper pKa values.

In one aspect, the "linking" hydroxyl group, i.e., the hydroxyl group of the drug that is used to conjugate the drug to the aminobenzyl group, is attached to an aromatic ring. Typically, hydroxyl groups that are attached to aromatic rings have greater acidity than hydroxyl groups that are attached to an aliphatic group. Perhaps for this reason, drugs with aromatic ring-bound hydroxyl groups typically tend to decompose more rapidly than drugs with aliphatic bound hydroxyl groups in the conjugates of the present invention. Nevertheless, in one aspect of the invention, the hydroxyl group that links the drug to the conjugate is bonded to an aliphatic carbon of the drug.

Factors other than the acidity of a hydroxyl group may be important in describing the kinetics of the decomposition process. Another factor to be considered is the steric strain of the conjugate. In general, as the drug is more sterically confined by being conjugated in the prodrug form, the drug will more readily separate from the prodrug form upon decomposition of the aminobenzyl ether group.

Yet another factor to consider is the substitution on the aromatic ring of the aminobenzyl ether group, i.e., the choice of the J group. As that substitution is better able to stabilize the decomposition product and/or destabilize the drug conjugate, the substitution will be able to promote the decomposition process. Thus, with drugs that have relatively unstable D-O⁻ forms, and/or that are not sterically strained in the prodrug form, it is preferred to select substitution for the aromatic ring of the aminobenzyl ether group such that the prodrug will more quickly decompose under the desired in vivo or in vitro conditions.

In one aspect, the drug used in the present invention is a cytotoxic drug, and particularly a cytotoxic drug that has demonstrated efficacy in cancer therapy. Representatives of such drugs are minor groove binders (MGBs), and MGB derivatives or analogs such as alkylated MGBs. Representative minor groove binders that may be formed into prodrugs according to the present invention include, without limitation, U-76,073, which has the chemical name (S)—N-[2-[[1-(chloromethyl)-1,6-dihydro-5-hydroxy-8-methylbenzo[1,2-b:4,3-b']dipyrrol-3(2yl]carbonyl]-1H-indol-5-yl]-6-(diethylamino)-2-benzofurancarboxamide; seco-adozelesin; bizelesin; 1,2,9,9a-tetra-hydro-cyclo-propa[c]-benz[e]indol-4-one-trimethoxyindole (CBI-TMI); duocarmycin C2; duocarmycin B2; and seco-CC-1065, which has the chemical name benzo(1,2-b:4,3-b')dipyrrole-3(2H)-carboxamide, 7-((1,6-dihydro-4-hydroxy-5-methoxy-7-((4,5,8,8a-tetrahydro-7-methyl-4-oxocyclopropa(c)pyrrolo(3,2-e)indol-2 (1H)-yl)carbonyl)benzo(1,2-b:4,3-b')dipyrrol-3(2H)-yl)carbonyl)-1,6-dihydro-4-hydroxy-5-methoxy-, (7bR).

Representative derivatives and analogs of MGBs include, without limitation, alkylated minor groove binders such as 1,2,9,9a-tetra-hydro-cyclo-propa[c]benz[e]indol-4-one (CBI) conjugated to an MGB; cyclopropapyrroloindole (CPI) conjugated to an MGB; and 1,2,9,9a-tetra-hydro-cyclo-propa [c]pyrido[3,2-e]indol-4-one (CPyI) conjugated to an MGB.

Another preferred group of cytotoxic agents for use as drugs in the present invention include, without limitation, etoposide; combretastatin A-4; pancratistatin; caminomycin; streptonigrin; zorubicin; elliptinium acetate; mitoxantrone; daunorubicin; phenol mustard; doxorubicin; and 7-ethyl-10-hydroxycamptothecin (SN-38). These drugs, along with the minor groove binders are represented by the formulas shown in FIGS. 2A-2E.

Another preferred drug is auristatin E, (see U.S. Pat. No. 5,635,483), as shown below:

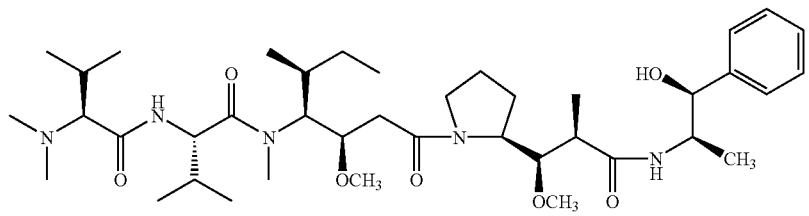

Auristatin E

In the drug conjugates of formula I and II, when a second self-immolative spacer (W) is present, D is a drug containing a chemically reactive functional group by means of which the drug is bonded to the peptide linker. The range of suitable reactive groups increases when "W" is present in a drug-conjugate of the invention. Said functional group may be selected from primary or secondary amine, hydroxyl, sulfhydryl, carboxyl, aldehyde and ketone.

Representative of said amino containing drugs are mitomycin-C, mitomycin-A, daunorubicin, doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, cytarabine and derivatives thereof. (See, U.S. Pat. No. 6,214,345). Other representative amino containing drugs are amino substituted CBI compounds, as shown by the following formulas:

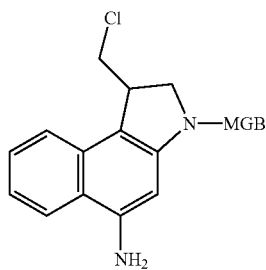 (IXa)

5-amino-CBI conjugated to an MGB

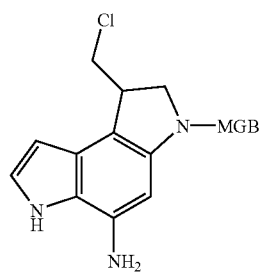 (IXb)

5-amino-CPI conjugated to an MGB

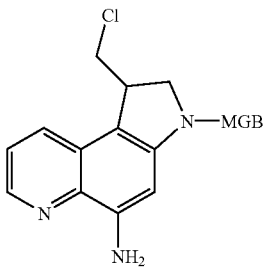 (IXc)

5-amino-CPyI conjugated to an MGB

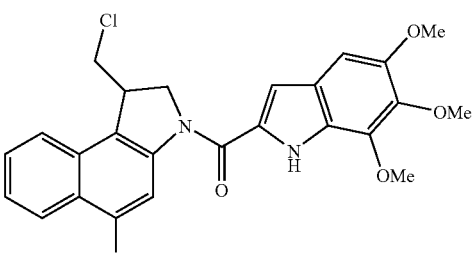 (IXb)

5-amino-CBI-TMI

Representative of said hydroxyl containing drugs are etoposide, camptothecin, taxol, esperamicin, 1,8-dihydroxy-bicyclo[7.3.1] trideca-4-9-diene-2,6-diyne-13-one, (U.S. Pat. No. 5,198,560), podophyllotoxin, anguidine, vincristine, vinblastine, morpholine-doxorubicin, N-(5,5-diacetoxy-pentyl) doxorubicin, auristatin E, and derivatives thereof.

Representative of said sulfhydryl containing drugs are esperamicin and 6-mercaptopurine, and derivatives thereof. Representative of said carboxyl containing drugs are methotrexate, camptothecin (ring-opened form of the lactone), butyric acid, retinoic acid, and derivatives thereof.

Representative of said aldehyde and ketone containing drugs are anguidine and anthracyclines such as doxorubicin, and derivatives thereof.

5.3. The Ligand

The ligand (L) can be any molecule that binds to, complexes with or reacts with a moiety of a cell population sought to be therapeutically or otherwise biologically modified. The ligand acts to deliver the drug to the particular target cell population with which the ligand reacts. Such ligands include, but are not limited to, large molecular weight proteins such as, for example, full-length antibodies, antibody fragments, smaller molecular weight proteins, polypeptide or peptides, and lectins.

In one embodiment, the ligand is an antibody.

A ligand can form a bond to either an acyl unit (A) or an Amino Acid or peptide (Z). A ligand can form a bond to a prodrug linker via a heteroatom of the ligand. Heteroatoms that may be present on a ligand include sulfur (in one embodiment, from a sulfhydryl group of a ligand), oxygen (in one embodiment, from a carbonyl, carboxyl or hydroxyl group of a ligand) and nitrogen (in one embodiment, from a primary or secondary amino group of a ligand). These heteroatoms can be present on the ligand in the ligand's natural state, for example a naturally occurring antibody, or can be introduced into the ligand via chemical modification.

In a preferred embodiment, a ligand has a sulfhydryl group and the ligand bonds to the prodrug linker via the sulfhydryl group's sulfur atom.

In another embodiment, the ligand can have one or more carbohydrate groups that can be chemically modified to have one or more sulfhydryl groups. The ligand bonds to the prodrug linker via the sulfhydryl group's sulfur atom.

In yet another embodiment, the ligand can have one or more carbohydrate groups that can be oxidized to provide an aldehyde (—CHO) group (see Laguzza, et al., *J. Med. Chem.* 1989, 32(3), 548-55). The corresponding aldehyde can form a bond with a terminal amino group present on group Z of the prodrug linker.

Useful non-immunoreactive protein, polypeptide, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Useful Polyclonal antibody ligands are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

In one embodiment, the ligand is a monoclonal antibody.

Useful monoclonal antibody ligands are homogeneous populations of antibodies to a particular antigen (e.g., a cancer cell antigen, a viral antigen, a microbial antigen covalently linked to a second molecule). A monoclonal antibody (mAb) to an antigen-of-interest can be prepared by using any technique known in the art which provides for the production of antibody molecules by continuous cell lines in culture. These include, but are not limited to, the hybridoma technique originally described by Kohler and Milstein (1975, *Nature* 256, 495-497), the human B cell hybridoma technique (Kozbor et al., 1983, *Immunology Today* 4: 72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibody ligands include, but are not limited to, human monoclonal antibodies or chimeric human-mouse (or other species) monoclonal antibodies. Human monoclonal antibodies may be made by any of numerous techniques known in the art (e.g., Teng et al., 1983, *Proc. Natl. Acad. Sci. U.S.A.* 80, 7308-7312; Kozbor et al., 1983, *Immunology Today* 4, 72-79; and Olsson et al., 1982, *Meth. Enzymol.* 92, 3-16).

The ligand can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually performed using affinity chromatography steps, is rather cumbersome, and the product yields are low. Similar procedures are disclosed in International Publication No. WO 93/08829, and in Traunecker et al., *EMBO J.* 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., *Methods in Enzymology*, 1986, 121:210. Using such techniques, bispecific antibody ligands can be prepared for use in the treatment or prevention of disease as defined herein.

Bifunctional antibodies are also described, in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The ligand can be a functionally active fragment, derivative or analog of an antibody that immunospecifically binds to cancer cell antigens, viral antigens, or microbial antigens. In this regard, "Functionally active" means that the fragment, derivative or analog is able to elicit anti-anti-idiotype antibodies that recognize the same antigen that the antibody from which the fragment, derivative or analog is derived recognized. Specifically, in a preferred embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay)

Other useful ligands include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful ligands are heavy chain and light chain dimers of antibodies, or any minimal fragment thereof such as Fvs or single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful ligands. A chimeric antibody is a molecule in which different portions are derived from different animal species, such as those having a variable region derived from a murine monoclonal and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 184,187; European Patent Publication No. 171,496; European Patent Publication No. 173,494; International Publication No. WO 86/01533; U.S. Pat. No. 4,816,567; European Patent Publication No. 125,023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Canc. Res.* 47:999-1005; Wood et al., 1985, *Nature* 314:446-449; and Shaw et al., 1988, *J. Natl. Cancer Inst.* 80:1553-1559; Morrison, 1985, *Science* 229: 1202-1207; Oi et al., 1986, *BioTechniques* 4:214; U.S. Pat. No. 5,225,539; Jones et al., 1986, *Nature* 321:552-525; Verhoeyan et al. (1988) *Science* 239:1534; and Beidler et al., 1988, *J. Immunol.* 141:4053-4060; each of which is incorporated herein by reference in its entirety.

Completely human antibodies are particularly desirable for ligands. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Biotechnology* 12:899-903).

In other embodiments, the ligand is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the N-terminus of the constant domain.

The ligand antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formulation, metabolic synthesis of tunicamycin, etc. Additionally, the analog or derivative can contain one or more unnatural amino acids.

The ligand antibodies include antibodies having modifications (e.g., substitutions, deletions or additions) in amino acid residues that interact with Fc receptors. In particular, the ligand antibodies include antibodies having modifications in amino acid residues identified as involved in the interaction between the Fc domain and the FcRn receptor (see, e.g., International Publication No. WO 97/34631, which is incorporated herein by reference in its entirety). Antibodies immunospecific for a cancer cell antigen can be obtained commercially, for example, from Genentech (San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention of cancer are used in accordance with the compositions and methods of the invention. Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, HERCEPTIN (Trastuzumab; Genentech, CA) which is a humanized anti-HER2 monoclonal antibody for the treatment of patients with metastatic breast cancer (Stebbing, J., Copson, E., and O'Reilly, S. "Herceptin (trastuzamab) in advanced breast cancer" *Cancer Treat Rev.* 26, 287-90, 2000); RITUXAN (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; BEC2 (ImClone Systems Inc., NY) which is murine IgG antibody for the treatment of lung cancer; IMC-C225 (Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart MI95 (Protein Design Labs, Inc., CA) which is a humanized IgG antibody for the treatment of acute myeloid leukemia (AML); LymphoCide (Immunomedics, Inc., NJ) which is a humanized IgG antibody for the treatment of non-Hodgkin's lymphoma; Smart ID10 (Protein Design Labs, Inc., CA) which is a humanized antibody for the treatment of non-Hodgkin's lymphoma; Oncolym (Techniclone, Inc., CA) which is a murine antibody for the treatment of non-Hodgkin's lymphoma; Allomune (BioTransplant, CA) which is a humanized anti-CD2 mAb for the treatment of Hodgkin's Disease or non-Hodgkin's lymphoma; anti-VEGF (Genentech, Inc., CA) which is humanized antibody for the treatment of lung and colorectal cancers; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone, NJ) which is an anti-EGFR chimeric antibody for the treatment of epidermal growth factor positive cancers.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific useful antibodies include, but are not limited to, BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" *Science* 1993, 261, 212-215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" *Cancer Research* 1997, 57, 100-105, mAbs against the CD 40 antigen, such as S2C6 mAb (Francisco, J. A., Donaldson, K. L., Chace, D., Siegall, C. B., and Wahl, A. F.

"Agonistic properties and in vivo antitumor activity of the anti-CD-40 antibody, SGN-14" *Cancer Res.* 2000, 60, 3225-3231), and mAbs against the CD30 antigen, such as AC10 (Bowen, M. A., Olsen, K. J., Cheng, L., Avila, D., and Podack, E. R. "Functional effects of CD30 on a large granular lymphoma cell line YT" *J. Immunol.*, 151, 5896-5906, 1993). Many other internalizing antibodies that bind to tumor associated antigens can be used in this invention, and have been reviewed (Franke, A. E., Sievers, E. L., and Scheinberg, D. A., "Cell surface receptor-targeted therapy of acute myeloid leukemia: a review" *Cancer Biother Radiopharm.* 2000, 15, 459-76; Murray, J. L., "Monoclonal antibody treatment of solid tumors: a coming of age" *Semin Oncol.* 2000, 27, 64-70; Breitling, F., and Dubel, S., *Recombinant Antibodies*, John Wiley, and Sons, New York, 1998).

In another specific embodiment, known antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university scientist or a company such as Genentech) or produced by any method known to one of skill in the art such as, e.g., chemical synthesis or recombinant expression techniques. In another embodiment, useful ligand antibodies that are immunospecific for the treatment of autoimmune diseases include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-U1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody.

In certain preferred embodiments, antibodies useful in the present methods, can bind to both a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the ligand is an antibody that binds to an activated lymphocyte that is associated with an autoimmune disease.

In another embodiment, the ligand is a monoclonal antibody against a T-cell activating antigen, such as CD30.

In another specific embodiment, useful ligand antibodies that are immunospecific for a viral or a microbial antigen are monoclonal antibodies. Preferably, ligand antibodies that are immunospecific for a viral antigen or microbial antigen are humanized or human monoclonal antibodies. As used herein, the term "viral antigen" includes, but is not limited to, any viral peptide, polypeptide protein (e.g., HIV gp120, HIV nef, RSV F glycoprotein, influenza virus neuramimidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from Genentech (San Francisco, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, the literature publications, or by routine cloning and sequencing.

In a specific embodiment, useful ligand antibodies are those that are useful for the treatment or prevention of viral or microbial infection in accordance with the methods of the invention. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG$_1$ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma spp., Rickettsia prowazeki, Rickettsia tsutsugumushi, Chlamydia spp.*); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picomaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

The antibodies suitable for use in the invention can be produced by any method known in the art for the synthesis of antibodies, in particular, by chemical synthesis or by recombinant expression, and are preferably produced by recombinant expression techniques.

5.3.1. Production of Recombinant Antibodies

Ligand antibodies of the invention can be produced using any method known in the art to be useful for the synthesis of antibodies, in particular, by chemical synthesis or by recombinant expression, and are preferably produced by recombinant expression techniques.

Recombinant expression of the ligand antibodies, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing an animal, such as a rabbit, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody can be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; International Publication No. WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis and in vitro site directed mutagenesis (Hutchinson et al., 1978, J. Biol. Chem. 253:6551).

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038-1041).

Antibody fragments that recognize specific epitopes can be generated by known techniques. For example, such fragments include, but are not limited to, the F(ab')2 fragments that can be produced by pepsin digestion of the antibody molecule and the Fab fragments that can be generated by reducing the disulfide bridges of the F(ab')2 fragments.

Once a nucleic acid sequence encoding a ligand antibody has been obtained, the vector for the production of the antibody can be produced by recombinant DNA technology using techniques well known in the art. Methods that are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

An expression vector comprising the nucleotide sequence of an antibody or the nucleotide sequence of an antibody can be transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

The host cells used to express the recombinant ligand antibody can be either bacterial cells such as Escherichia coli, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 198, Gene 45:101; Cockett et al., 1990, BioTechnology 8:2).

A variety of host-expression vector systems can be utilized to express the immunoglobulin ligands. Such host-expression systems represent vehicles by which the coding sequences of the antibody can be produced and subsequently purified, but also represent cells that can, when transformed or transfected with the appropriate nucleotide coding sequences, express a ligand immunoglobulin molecule in situ. These include, but are not limited to, microorganisms such as bacteria (e.g., E. coli and B. subtilis) transformed with recombinant bacteriophage DNA, plasmid DNA or cosmid DNA expression vectors containing immunoglobulin coding sequences; yeast (e.g., Saccharomyces Pichia) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited to, the E. coli expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) or the analogous virus from Drosophila Melanogaster is used as a vector to express foreign genes. The virus grows in Spodoptera frugiperda cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (e.g., see Logan & Shenk, 1984, Proc. Natl. Acad. Sci. USA 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, Methods in Enzymol. 153:51-544).

In addition, a host cell strain can be chosen to modulate the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERY, BH, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody Such engineered cell lines can be particularly useful in screening and evaluation of tumor antigens that interact directly or indirectly with the antibody ligand.

A number of selection systems can be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260: 926-932; and Morgan and Anderson, 1993, Ann. Rev. Biochem. 62:191-217; May, 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

The expression levels of an antibody can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell. Biol. 3:257).

The host cell can be co-transfected with two expression vectors of the invention, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used to encode both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains can comprise cDNA or genomic DNA.

Once the antibody has been recombinantly expressed, it can be purified using any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

In any case, the hybrid antibodies have a dual specificity, preferably with one or more binding sites specific for the hapten of choice or one or more binding sites specific for a target antigen, for example, an antigen associated with a tumor, an autoimmune disease, an infectious organism, or other disease state.

5.4. Preparation of the Conjugates

The peptide derivative, Cbz-valine-citrulline-p-aminobenzyl alcohol (1, Cbz-val-cit-PAB-OH) has previously been used for the preparation of Cbz-val-cit-PAB-doxorubicin carbamate, a compound that released active doxorubicin upon treatment with cathepsin B (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341-3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347-3352). The drug was attached to the peptide through a carbamate linkage as shown in Scheme 2 (Y=NH).

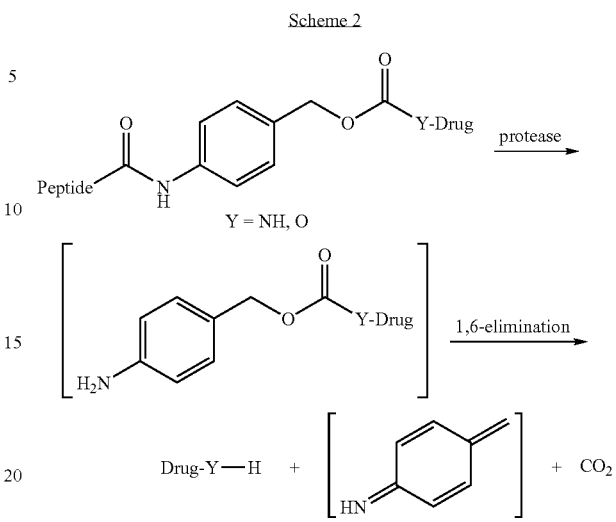

To explore the potential of using this drug elimination pathway for cleaving less labile bonds, ether derivatives of 1 were prepared using either the Mitsunobu reaction to form the naphthol ether 2, or the two-step imidate-substitution reaction to form the N-acetylnorephedrine derivative 5 (Scheme 3).

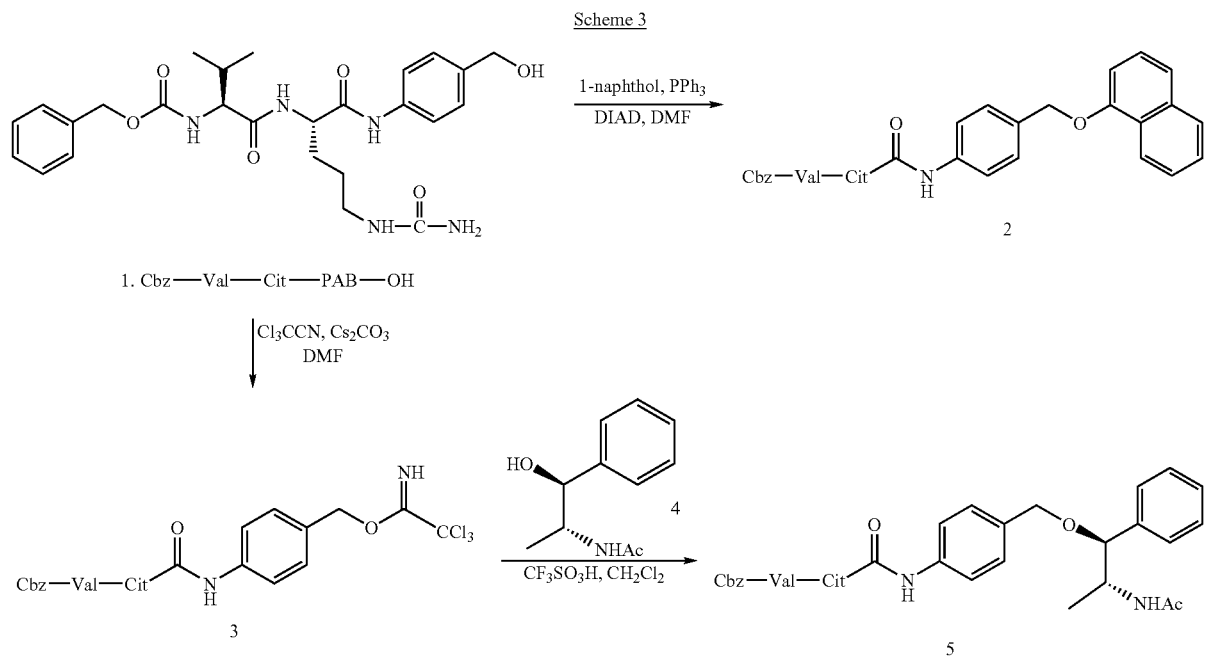

These compounds were designed to model anticancer drugs that contain chemically related moieties. HPLC analysis indicated that the naphthol ether 2 was a substrate for bovine spleen cathepsin B, and that the products formed were naphthol and Cbz-val-cit-COOH. The reaction proceeded rapidly (350 nmol/min/mg cathepsin B), but in the absence of added enzyme there was no breakdown of the starting material after 1 week at 37° C. at pH 5.1, 7.2, and in pooled human serum (Table I). The present invention provides the first indication that p-aminobenzyl ethers are capable of undergoing 1,6-elimination reactions.

Similar studies undertaken with the N-acetylnorephedrine ether 5 demonstrated that the compound was hydrolyzed by cathepsin B, leading to the release of Cbz-val-cit-COOH as expected. However, no N-acetylnorephedrine was detected, suggesting that the p-aminobenzyl ether formed after peptide bond cleavage did not undergo further fragmentation. Thus, the nature of the leaving group attached to the p-aminobenzyl group affects the 1,6-elimination reaction. It is speculated, however, that a more electron negative substituent at the α position of the hydroxyl group may facilitate the fragmentation. For example, if —NHAc is replaced by —F, the inductive effect of the strongly electron negative group F is capable of stabilizing the intermediate conjugate base resulted from the fragmentation.

On the basis of these results, the anticancer drugs etoposide (VIIIa) and combretastatin A-4 (VIIIb) were linked to 1 using the coupling conditions shown in Scheme 4.

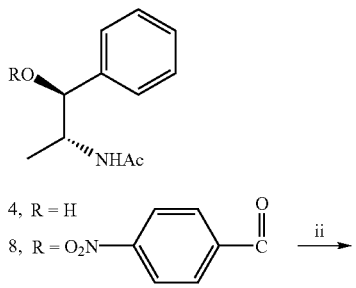

Etoposide is a clinically approved topoisomerase inhibitor that has demonstrated utility in chemotherapeutic combinations for the treatment of leukemia, lymphoma, germ cell tumors, small cell lung tumors and several other carcinomas (Hande, K. R. Etoposide: Four Decades of Development of a Topoisomerase II Inhibitor. *Eur J Cancer* 1998, 34, 1514-1521). Combretastatin A-4 is a promising antiangiogenic agent that inhibits the polymerization of tubulin (Horsman, M. R.; Murata, R.; Breidahl T.; Nielson, F. U.; Maxwell, R. J.; Stodkiled-Horgensen, H.; Overgaard. Combretastatins Novel Vascular Targeting Drugs for Improving Anti-Cancer Therapy. Combretastatins and Conventional Therapy. *J. Adv. Exp. Med. Biol.* 2000, 476, 311-323). Treatment of 6 and 7 with cathepsin B led to the release of etoposide (VIIIa) and combretastatin A-4 (VIIIb), respectively (Table I). Both peptide derivatives were stable at pH 5.1, 7.2, and in human serum.

For comparison, the carbonate derivatives 10 and 11 were prepared from acetylnorephedrine (4) and combretastatin A-4 (VIIIb), respectively (Scheme 5).

-continued

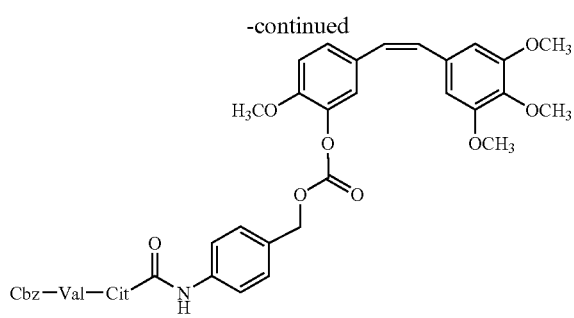

11 i. p-nitrophenylchloroformate, pyridine, DCM.
ii. 1, DMAP, DCM

Both carbonates 10 and 11 proved to be unstable in aqueous environments, in contrast to the corresponding ethers 5 and 7, respectively.

As expected enzymatic hydrolysis of 10 and 11 led to the formation of 4 and VIIIb. It is noteworthy that there were no significant kinetic differences in cathepsin B mediated hydrolyses of the peptide-carbonate and peptide-ether derivatives. Thus, peptide derivatives of p-aminobenzyl aromatic ethers are stable in neutral or slightly acidic buffers, and undergo facile ether fragmentation upon treatment with an enzyme that cleaves the amide bond.

In vitro cytotoxicity were performed on cancer cell lines to determine if the peptide derivatives acted as prodrugs. The cell lines (L2987 human lung adenocarcinoma, WM266/4 and IGR-39 human melanomas) were exposed to the agents for 24 h, washed, and viability was determined two days later by measuring the incorporation of $^3$H-thymidine compared to the untreated controls. There were significant differences in the cytotoxic activity etoposide (VIIIa) and the corresponding peptide ether derivative (6) on all three cell lines (FIGS. 1A-C). Etoposide (VIIIa) was 15-22 times more active than 6, a result consistent with the loss in cytotoxic activity that has been reported with another phenol derivatives of etoposide (Senter, P. D.; Saulnier, M. G.; Schreiber, G. J.; Hirschberg, D. L.; Brown, J. P.; Hellström, I.; Hellström, K. E. Anti-Tumor Effects of Antibody-Alkaline Phosphatase Conjugates in combination with Etoposide Phosphate. Proc. Natl. Acad. Sci. USA 1988, 85, 4842-4846). Similarly, the combretastatin ether (7) was less potent than combretastatin A-4 (VIIIb) by a factor of 13 on L2987 human lung adenocarcinoma cells (FIG. 1D). Significantly, the combretastatin A-4 carbonate derivative 11 was as cytotoxic as combretastatin A-4 (VIIIb), reflecting the inherent instability of carbonate compared to the ether linkages (Table I). These results, taken together with the enzyme hydrolysis studies, indicate that the peptide ether drug derivatives are prodrugs that can be activated by cathepsin B.

5.5. Compositions

In other aspects, the present invention provides prodrugs comprising a novel aminobenzyl ether spacer as described above, in combination with a pharmaceutically acceptable carrier, excipient, or diluent. Thus, the present invention provides a pharmaceutical or veterinary composition (hereinafter, simply referred to as a pharmaceutical composition) containing a prodrug of the invention as described above, in admixture with a pharmaceutically acceptable carrier. The invention further provides a composition, preferably a pharmaceutical composition, containing an effective amount of a prodrug as described above, in association with a pharmaceutically acceptable carrier.

The pharmaceutical compositions of the present invention may be in any form that allows for the composition to be administered to an animal subject. For example, the composition may be in the form of a solid, liquid or gas (aerosol). Typical routes of administration include, without limitation, oral, topical, parenteral, sublingual, rectal, vaginal, ocular, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to an animal subject. Compositions that will be administered to a subject take the form of one or more dosage units, where for example, a tablet may be a single dosage unit, and a container of a compound of the invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration, and the composition employed.

In general, the pharmaceutical composition includes an (where "a" and "an" refers here, and throughout this specification, as one or more) active compounds of the invention in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin, or a fatty oil.

The composition may be in the form of a liquid, e.g., an elixir, syrup, solution, emulsion, or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition for administration by injection, one or more of a surfactant, preservative, wetting agent, dispersing agent, suspending agent, buffer, stabilizer, and isotonic agent may be included.

The liquid pharmaceutical compositions of the invention, whether they are solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of the present invention such that a suitable dosage will be obtained. Typically, this amount is at least 0.01% of a compound of the invention in the composition however the precise dose will depend in large part on the drug selected for incorporation into the inventive conjugates. When intended for oral administration, this amount may be varied to be between 0.1% and about 80% of the weight of the composition. Preferred oral compositions contain between about 4% and about 50% of the compound of the invention. Preferred compositions and preparations according to the present invention are prepared so that a parenteral dosage unit contains between 0.01% to 2% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of a compound of the present invention of from about 0.1% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of cancer.

The pharmaceutical compositions may be prepared by methodology well known in the pharmaceutical art. For example, a composition intended to be administered by injection can be prepared by combining a compound of the invention with water so as to form a solution. A surfactant may be added to facilitate the formation of a homogeneous solution or suspension. Surfactants are compounds that non-covalently interact with a compound of the invention so as to facilitate dissolution or homogeneous suspension of the active compound in the aqueous delivery system.

5.6 Therapeutic uses of the Compounds of the Invention

The present invention provides biologically-active compounds, and methods of preparing the compounds of the invention, pharmaceutical compositions comprising the compounds of the invention, and methods for treatment of cancers and other tumors in animal subjects. For instance, the invention provides compounds and compositions for use in a method for treating tumors wherein the animal subject is treated, in a pharmaceutically acceptable manner, with a pharmaceutically effective amount of a compound or composition of the present invention.

The Compounds of the Invention are useful for treating cancer, an autoimmune disease or an infectious disease in an animal.

5.7. Treatment of Cancer

The Compounds of the Invention are useful for inhibiting the multiplication of a tumor cell or cancer cell, or for treating cancer in an animal. The Compounds of the Invention can be used accordingly in a variety of settings for the treatment of animal cancers. The drug conjugates can be used to deliver a drug to a tumor cell or cancer cell. Without being bound by theory, in one embodiment, the ligand of a Compound of the Invention binds to or associates with a cancer-cell or a tumor-cell-associated antigen, and the Compound of the Invention can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the linker are hydrolytically cleaved by one or more tumor-cell or cancer-cell-associated proteases, resulting in release of a drug. The released drug is then free to migrate in the cytosol and induce cytotoxic activities. In an alternative embodiment, the drug is cleaved from the Compound of the Invention outside the tumor cell or cancer cell, and the drug subsequently penetrates the cell.

In one embodiment, the ligand binds to the tumor cell or cancer cell.

In another embodiment, the ligand binds to a tumor cell or cancer cell antigen which is on the surface of the tumor cell or cancer cell.

In another embodiment, the ligand binds to a tumor cell or cancer cell antigen which is an extracellular matrix protein associated with the tumor cell or cancer cell.

In one embodiment, the tumor cell or cancer cell is of the type of tumor or cancer that the animal needs treatment or prevention of.

The specificity of the ligand for a particular tumor cell or cancer cell can be important for determining those tumors or cancers that are most effectively treated. For example, Compounds of the Invention having a BR96 ligand can be useful for treating antigen positive carcinomas including those of the lung, breast, colon, ovaries, and pancreas. Compounds of the Invention having an Anti-CD30 or an anti-CD40 ligand can be useful for treating hematologic malignancies.

Other particular types of cancers that can be treated with Compounds of the Invention include, but are not limited to, those disclosed in Table 1.

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophogeal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma TABLE 1-continued glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma blood-borne cancers, including but not limited to:

acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma acute and chronic leukemias:

lymphoblastic
myelogenous
lymphocytic
myelocytic leukemias

Lymphomas:

Hodgkin's disease
non-Hodgkin's Lymphoma
Multiple myeloma
Waldenström's macroglobulinemia
Heavy chain disease
Polycythemia vera The Compounds of the Invention can also be used as chemotherapeutics in the untargeted form. For example, the Drugs themselves are useful for treating ovarian, CNS, renal, lung, colon, melanoma, or hematologic cancers or tumors.

The Compounds of the Invention provide Conjugation specific tumor or cancer targeting, thus reducing general toxicity of these compounds. The linker stabilize the Compounds of the Invention in blood, yet are cleavable by tumor-specific proteases within the cell, liberating a Drug.

5.7.1. Multi-Modality Therapy for Cancer

Cancer, or a precancerous condition, including, but not limited to, a tumor, metastasis, or any disease or disorder characterized by uncontrolled cell growth, can be treated or prevented by administration of a Compound of the Invention.

In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy.

In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 4 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

5.7.2. Multi-Drug Therapy for Cancer

The present invention includes methods for treating cancer, comprising administering to an animal in need thereof an effective amount of a Compound of the Invention and another therapeutic agent that is an anti-cancer agent. Suitable anti-cancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, the anti-cancer agent includes, but is not limited to, a drug listed in Table 2.

TABLE 2

| | |
|---|---|
| Alkylating agents | |
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum containing compounds: | Cisplatin |
| | Carboplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxol |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| mitomycins: | Mitomycin C |
| | Anti-metabolites |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | Deferoxamine |
| Pyrimidine analogs: | |
| Uracil analogs: | 5-Fluorouracil |
| | Floxuridine |
| | Doxifluridine |
| | Ratitrexed |
| Cytosine analogs: | Cytarabine (ara C) |
| | Cytosine arabinoside |
| | Fludarabine |
| Purine analogs: | Mercaptopurine |
| | Thioguanine |
| Hormonal therapies: | |
| Receptor antagonists: | |
| Anti-estrogen: | Tamoxifen |
| | Raloxifene |
| | Megestrol |
| LHRH agonists: | Goscrclin |
| | Leuprolide acetate |
| Anti-androgens: | Flutamide |
| | Bicalutamide |
| Retinoids/Deltoids | |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A |
| | (2BA-2-DMHA) |
| Cytokines: | Interferon- α |
| | Interferon- γ |
| | Tumor necrosis factor |
| Others: | |
| Isoprenylation inhibitors: | Lovastatin |
| Dopaminergic neurotoxins: | 1-methyl-4-phenylpyridinium ion |

TABLE 2-continued

| | |
|---|---|
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

5.8. Treatment of Autoimmune Diseases

The Compounds of the Invention are useful for killing or inhibiting the replication of a cell that produces an autoimmune disease or for treating an autoimmune disease. The Compounds of the Invention can be used accordingly in a variety of settings for the treatment of an autoimmune disease in an animal. The drug conjugates can be used to deliver a drug to a target cell. Without being bound by theory, in one embodiment, the drug conjugate associates with an antigen on the surface of a target cell, and the Compound of the Invention is then taken up inside a target-cell through receptor-mediated endocytosis. Once inside the cell, one or more specific peptide sequences within the linker are enzymatically or hydrolytically cleaved, resulting in release of a drug. The released drug is then free to migrate in the cytosol and induce cytotoxic activities. In an alternative embodiment, the drug is cleaved from the Compound of the Invention outside the target cell, and the drug subsequently penetrates the cell.

In one embodiment, the ligand binds to an autoimmune antigen.

In another embodiment, the ligand binds to an autoimmune antigen which is on the surface of a cell.

In another embodiment, the target cell is of the type of cell that produces the autoimmune antigen which causes the disease the animal needs treatment or prevention of.

In a preferred embodiment, the ligand binds to activated lymphocytes that are associated with the autoimmune disease state.

In a further embodiment, the Compounds of the Invention kill or inhibit the multiplication of cells that produce an autoimmune antibody associated with a particular autoimmune disease.

Particular types of autoimmune diseases that can be treated with the Compounds of the Invention include, but are not limited to, Th2-lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 3.

TABLE 3

Active Chronic Hepatitis
Addison's Disease
Allergic Alveolitis
Allergic Reaction
Allergic Rhinitis
Alport's Syndrome
Anaphlaxis
Ankylosing Spondylitis
Anti-phosholipid Syndrome
Arthritis
Ascariasis
Aspergillosis
Atopic Allergy
Atropic Dermatitis
Atropic Rhinitis
Behcet's Disease
Bird-Fancier's Lung
Bronchial Asthma
Caplan's Syndrome
Cardiomyopathy
Celiac Disease
Chagas' Disease
Chronic Glomerulonephritis
Cogan's Syndrome
Cold Agglutinin Disease
Congenital Rubella Infection
CREST Syndrome
Crohn's Disease
Cryoglobulinemia
Cushing's Syndrome
Dermatomyositis
Discoid Lupus
Dressler's Syndrome
Eaton-Lambert Syndrome
Echovirus Infection
Encephalomyelitis
Endocrine opthalmopathy
Epstein-Barr Virus Infection
Equine Heaves
Erythematosis
Evan's Syndrome
Felty's Syndrome
Fibromyalgia
Fuch's Cyclitis
Gastric Atrophy
Gastrointestinal Allergy
Giant Cell Arteritis
Glomerulonephritis
Goodpasture's Syndrome
Graft v. Host Disease
Graves' Disease
Guillain-Barre Disease
Hashimoto's Thyroiditis
Hemolytic Anemia
Henoch-Schonlein Purpura
Idiopathic Adrenal Atrophy
Idiopathic Pulmonary Fibritis
IgA Nephropathy
Inflammatory Bowel Diseases
Insulin-dependent Diabetes Mellitus
Juvenile Arthritis
Juvenile Diabetes Mellitus (Type I)
Lambert-Eaton Syndrome
Laminitis
Lichen Planus
Lupoid Hepatitis
Lupus
Lymphopenia
Meniere's Disease
Mixed Connective Tissue Disease
Multiple Sclerosis
Myasthenia Gravis
Pernicious Anemia
Polyglandular Syndromes
Presenile Dementia
Primary Agammaglobulinemia
Primary Biliary Cirrhosis
Psoriasis
Psoriatic Arthritis

TABLE 3-continued

Raynauds Phenomenon
Recurrent Abortion
Reiter's Syndrome
Rheumatic Fever
Rheumatoid Arthritis
Sampter's Syndrome
Schistosomiasis
Schmidt's Syndrome
Scleroderma
Shulman's Syndrome
Sjorgen's Syndrome
Stiff-Man Syndrome
Sympathetic Ophthalmia
Systemic Lupus Erythematosis
Takayasu's Arteritis
Temporal Arteritis
Thyroiditis
Thrombocytopenia
Thyrotoxicosis
Toxic Epidermal Necrolysis
Type B Insulin Resistance
Type I Diabetes Mellitus
Ulcerative Colitis
Uveitis
Vitiligo
Waldenstrom's Macroglobulemia
Wegener's Granulomatosis

5.8.1. Multi-Drug Therapy of Autoimmune Diseases

The present invention also provides methods for treating an autoimmune disease, comprising administering to an animal in need thereof an effective amount of a Compound of the Invention and another therapeutic agent that known for the treatment of an autoimmune disease. In one embodiment, the anti-autoimmune disease agent includes, but is not limited to, agents listed in Table 4.

TABLE 4 cyclosporine
cyclosporine A
mycophenylate mofetil
sirolimus
tacrolimus
enanercept
prednisone
azathioprine
methotrexatecyclophosphamide
prednisone
aminocaproic acid
chloroquine
hydroxychloroquine
hydrocortisone
dexamethasone
chlorambucil
DHEA
danazol
bromocriptine
meloxicam
infliximab

5.9. Treatment of Infectious Diseases

The Compounds of the Invention are useful for killing or inhibiting the multiplication of a cell that produces an infectious disease or for treating an infectious disease. The Compounds of the Invention can be used accordingly in a variety of settings for the treatment of an infectious disease in an animal. The drug conjugates can be used to deliver a drug to a target cell. Without being bound by theory, in one embodiment, the drug conjugate associates with an antigen on the surface of a target cell, and the Compound of the Invention is then taken up inside a target-cell through receptor-mediated endocytosis. Once inside the cell, one or more specific peptide sequences within the linker are enzymatically or hydrolytically cleaved, resulting in release of a drug. The released drug is then free to migrate in the cytosol and induce cytotoxic activities. In an alternative embodiment, the drug is cleaved from the Compound of the Invention outside the target cell, and the drug subsequently penetrates the cell.

In one embodiment, the ligand binds to the infectious disease cell.

In one embodiment, the infectious disease type of infectious disease that the animal needs treatment or prevention of.

In one embodiment, the Compounds of the Invention kill or inhibit the multiplication of cells that produce a particular infectious disease.

Particular types of infectious diseases that can be treated with the Compounds of the Invention include, but are not limited to, those disclosed in Table 5.

TABLE 5

Bacterial Diseases:

Diptheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
Pneumococcal
Peritonitis
Bactermia
Meningitis
Acute Purulent Meningitis
Urethritis
Cervicitis
Proctitis
Pharyngitis
Salpingitis
Epididymitis
Gonorrhea
Syphilis
Listeriosis
Anthrax
Nocardiosis
Salmonella
Typhoid Fever
Dysentery
Conjuntivitis
Sinusitis
Brucellosis
Tullaremia
Cholera
Bubonic Plague
Tetanus
Necrotizing Enteritis
Actinomycosis
Mixed Anaerobic Infections
Syphilis
Relapsing Fever
Leptospirosis
Lyme Disease
Rat Bite Fever
Tuberculosis
Lymphadenitis
Leprosy

TABLE 5-continued

Chlamydia
Chlamydial Pneumonia
Trachoma
Inclusion Conjunctivitis
Systemic Fungal Diseases:

Histoplamosis
Coccicidiodomycosis
Blastomycosis
Sporotrichosis
Cryptococcsis
Systemic Candidiasis
Aspergillosis
Mucormycosis
Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection
Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease
Chickenpox
Respiratory syncytial virus infection
Croup
Bronchiolitis
Infectious Mononucleosis
Poliomyelitis
Herpangina

TABLE 5-continued

Hand-Foot-and-Mouth Disease
Bornholm Disease
Genital Herpes
Genital Warts
Aseptic Meningitis
Myocarditis
Pericarditis
Gastroenteritis
Acquired Immunodeficiency Syndrome (AIDS)
Reye's Syndrome
Kawasaki Syndrome
Influenza
Bronchitis
Viral "Walking" Pneumonia
Acute Febrile Respiratory Disease
Acute pharyngoconjunctival fever
Epidemic keratoconjunctivitis
Herpes Simplex Virus 1 (HSV-1)
Herpes Simples Virus 2 (HSV-2)
Shingles
Cytomegalic Inclusion Disease
Rabies
Progressive Multifocal Leukoencephalopathy
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox

5.9.1. Multi-Drug Therapy of Infectious Diseases

The present invention also provides methods for treating an infectious disease, comprising administering to an animal in need thereof a Compound of the Invention and another therapeutic agent that is an anti-infectious disease agent. In one embodiment, the anti-infectious disease agent is, but not limited to, agents listed in Table 6.

TABLE 6

Antibacterial Agents:
β-Lactam Antibiotics:

Penicillin G
Penicillin V
Cloxacilliin
Dicloxacillin
Methicillin
Nafcillin
Oxacillin
Ampicillin
Amoxicillin
Bacampicillin
Azlocillin
Carbenicillin
Mezlocillin
Piperacillin
Ticarcillin
Aminoglycosides:

Amikacin
Gentamicin

TABLE 6-continued

Kanamycin
Neomycin
Netilmicin
Streptomycin
Tobramycin
Macrolides:

Azithromycin
Clarithromycin
Erythromycin
Lincomycin
Clindamycin
Tetracyclines:

Demeclocycline
Doxycycline
Minocycline
Oxytetracycline
Tetracycline
Quinolones:

Cinoxacin
Nalidixic Acid
Fluoroquinolones:

Ciprofloxacin
Enoxacin
Grepafloxacin
Levofloxacin
Lomefloxacin
Norfloxacin
Ofloxacin
Sparfloxacin
Trovafloxicin
Polypeptides:

Bacitracin
Colistin
Polymyxin B
Sulfonamides:

Sulfisoxazole
Sulfamethoxazole
Sulfadiazine
Sulfamethizole
Sulfacetamide
Miscellaneous Antibacterial Agents:

Trimethoprim
Sulfamethazole
Chloramphenicol
Vancomycin
Metronidazole
Quinupristin
Dalfopristin
Rifampin
Spectinomycin
Nitrofurantoin
Antiviral Agents:
General Antiviral Agents:

Idoxuradine
Vidarabine
Trifluridine
Acyclovir
Famcicyclovir
Pencicyclovir
Valacyclovir
Gancicyclovir
Foscarnet
Ribavirin
Amantadine
Rimantadine
Cidofovir
Antisense Oligonucleotides
Immunoglobulins
Inteferons TABLE 6-continued Drugs for HIV infection:

Zidovudine
Didanosine
Zalcitabine
Stavudine
Lamivudine
Nevirapine
Delavirdine
Saquinavir
Ritonavir
Indinavir
Nelfinavir 5.10. Other Therapeutic Agents The present methods can further comprise the administration of a Compound of the Invention and an additional therapeutic agent or pharmaceutically acceptable salts or solvates thereof. The Compound of the Invention and the other therapeutic agent can act additively or, more preferably, synergistically. In a preferred embodiment, a composition comprising a Compound of the Invention is administered concurrently with the administration of one or more additional therapeutic agent(s), which can be part of the same composition or in a different composition from that comprising the Compound of the Invention. In another embodiment, a Compound of the Invention is administered prior to or subsequent to administration of another therapeutic agent(s).

In the present methods for treating cancer, an autoimmune disease or an infectious disease, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

The following examples are provided by way of illustration and not limitation.

6. EXAMPLES

General Methods. Commercially available reagents and solvents were obtained as follows: HPLC-grade solvents, Fisher; anhydrous solvents, Aldrich; diisopropyl azodicarboxylate (DIAD, 95%), Lancaster; 4-aminobenzyl alcohol, Alfa Aesar; Z-val-OSu, Advanced ChemTech; L-citrulline, Novabiochem; (1S, 2R)-(+)-norephedrine and other commercially available reagents, Aldrich. Cbz-val-cit-PAB-OH (1) (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341-3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347-3352) and combretastatin A-4 (VIIIb) (Pettit, G. R.; Singh, S. B.; Boyd, M. R.; Hamel, E.; Pettit, R. K.; Schmidt, J. M.; Hogan, F. Antineoplastic Agents. 291. Isolation and Synthesis of Combretastatin A-4, A-5, and A-6. *J. Med. Chem.* 1995, 38, 1666-1672) were synthesized as previously described. $^1$H NMR spectra were recorded on a Varian Gemini 300 MHz spectrophotometer. Flash column chromatography was performed using 230-400 mesh ASTM silica gel from EM Science. Analtech silica gel GHLF plates were used for thin-layer chromatography. HPLC was performed using a Waters Alliance system with a photodiode array detector. Combustion analyses were determined by Quantitative Technologies, Inc., Whitehouse, N.J.

General Procedure for the Mitsunobu Reaction. Peptide 1 (1.0 eq), triphenylphosphine (1.1 eq) and the appropriate phenol (1.0-1.1 eq) were dissolved in DMF/toluene (1:1) and evaporated to dryness under high vacuum. The residue was taken up in dry DMF while under $N_2$ and cooled to 0° C. DIAD (1.1 eq) was added dropwise over 1 min while stirring. The yellow/brown solution was monitored by TLC (9:1 $CH_2Cl_2$-MeOH). An additional 1.1 eq of $PPh_3$ and DIAD was added after 4 h. The solution was stirred for a total of 16-24 h, followed by solvent removal in vacuo. The resulting product was purified by chromatography on silica gel (eluent gradient: 100% $CH_2Cl_2$ to 9:1 $CH_2Cl_2$-MeOH). The desired fractions were pooled and concentrated to a white or off-white solid. Further purification could be obtained by triturating with ether.

Example 1

CBZ-VAL-CIT-PAB-1-O-NAPHTHOL (2).

$R_f$ 0.26 (9:1 $CH_2Cl_2$-MeOH); mp 175 (dec); UV $\lambda_{max}$ 215, 242, 305 nm; LRMS (ESI$^+$) m/z 640.3 (M+H)$^+$, 662.2 (M+Na)$^+$, 678.2 (M+K)$^+$; $^1$H NMR (DMSO-d$_6$) δ 8.19-8.24 (2H, m, aromatic), 7.80-7.87 (2H, m, aromatic), 7.06-7.50 (13H, m, aromatic), 6.76 (1H, d, J=7.8 Hz, aromatic), 5.07 (2H, s, Cbz-CH$_2$), 4.44-4.50 (1H, m, val-CH), 4.28 (2H, s, PAB-CH$_2$), 3.95 (1H, d, J=6.9 Hz, cit-CH), 3.03-3.20 (2H, m, cit-NCH$_2$), 1.95-2.10 (1H, m, val-CH), 1.28-1.178 (4H, m, cit-CH$_2$'s), 0.96 (3H, d, J=6.9 Hz, val-CH$_3$), 0.93 (3H, d, J=6.9 Hz, val-CH$_3$). Anal. ($C_{36}H_{41}N_5O_6 \cdot H_2O$) C, H, N.

Example 2

CBZ-VAL-CIT-PAB-O-TRICHLOROACETAMIDATE (3).

Peptide 1 (100 mg, 0.19 mmol) was dissolved in anhydrous DMF to which cesium carbonate (13 mg, 4 µmol, 0.2 eq) was added. While under $N_2$, trichloroacetonitrile (0.2 mL, 1.9 mmol, 10 eq) was added, and the contents stirred while monitoring by TLC (9:1 $CH_2Cl_2$-MeOH). Reaction was complete after 16 h. The mixture was filtered and filtrate concentrated and subject to chromatography on $SiO_2$ (eluent gradient 100% $CH_2Cl_2$ to 9:1 $CH_2Cl_2$-MeOH containing 1% triethylamine). The desired fractions were pooled and evaporated to an off-white powder (99 mg, 77%): $R_f$ 0.44 (9:1 $CH_2Cl_2$-MeOH); UV $\lambda_{max}$ 215, 250 nm; LRMS (ESI$^+$) m/z 679.3 (M+Na)$^+$, 681.2 (M+2+Na)$^+$, 683.2 (M+4+Na)$^+$, 685.2 (M+6+Na)$^+$, 695.2 (M+K)$^+$, 697.2 (M+2+K)$^+$, 699.2 (M+4+K)$^+$; $^1$H NMR (DMSO-d$_6$) δ 10.08 (1H, s, PAB-NH), 9.37 (1H, s, C=NH), 8.10 (1H, d, J=7.8 Hz, amide NH), 7.60 (2H, d, J=8.4 Hz, PAB-CH×2), 7.21-7.38 (8H, m, aromatic), 5.96 (1H, t, J=5.1 Hz, cit-NH), 5.40 (2H, s, cit-NH$_2$), 5.21 (2H, s, PAB-CH$_2$), 5.02 (2H, s, Cbz-CH$_2$), 4.40 (1H, dd, J=13.2, 7.8 Hz, val-CH), 3.90 (1H, t, J=8.4 Hz, cit-CH), 2.85-3.15 (2H, m, cit-CH$_2$), 1.90-2.05 (1H, m, val-CH), 1.28-1.74(4H, m, cit-CH$_2$), 0.86 (3H, d, J=6.6 Hz, val-CH$_3$), 0.82 (3H, d, J=6.9 Hz, val-CH$_3$). Anal. ($C_{28}H_{35}Cl_3N_6O_6 \cdot 0.2H_2O$, $0.4Et_3N$) C, H, N, Cl.

Example 3

(1S, 2R)-N-ACETYL-NOREPHEDRINE (4)

(1S, 2R)-(+)-norephedrine (5.0 g, 32.4 mmol) was partially suspended in water (65 mL, 0.5 M). Acetic anhydride (6.2 mL, 64.8 mmol, 2.0 eq) was added, and the resulting yellow solution was stirred for 1 h. EtOAc was added, the layers were separated, and the aqueous layer was further washed with EtOAc (2×). The combined extracts were washed with brine and dried (MgSO$_4$). Filtration, followed by removal of solvent led to a yellow oil that slowly formed yellow crystals. The crude product was purified by chromatography on $SiO_2$ (1:1 $CH_2Cl_2$-EtOAc) and the combined fractions were concentrated to a clear oil that solidified. Recrystallization from EtOAc-hexanes gave a white cotton-like solid as the desired product (4.95 g, 79%): mp 123 C; $R_f$ 0.14 (1:1 $CH_2Cl_2$-EtOAc); UV $\lambda_{max}$ 215, 256 nm; $^1$H NMR (CDCl$_3$) δ 7.28-7.39 (5H, m, aromatic), 5.59 (1H, br d, J=8.4 Hz, NH), 4.87 (1H, d, J=3.6 Hz, H-1), 4.34 (1H, dp, J=3.0, 6.9 Hz, H-2), 3.48 (1H, br s, OH), 2.01 (3H, s, Ac), 1.02 (3H, d, J=6.9 Hz, H-3). Anal. ($C_{11}H_{15}NO_2$) C, H, N.

Example 4

CBZ-VAL-CIT-PAB-O-(N-AC)-NOR (5)

The trichloroacetamidate 3 (1 eq) and alcohol 4 (1 eq) were suspended in anhydrous $CH_2Cl_2$ and cooled to 0 C. Dropwise addition of trifluoromethanesulfonic acid (0.5 eq) gave an immediate gummy precipitate. TLC analysis (9:1 $CH_2Cl_2$-MeOH) showed a product ($R_f$ 0.28) and some decomposition of 3 to Cbz-val-cit-PAB-OH 1 ($R_f$ 0.14). The contents were evaporated to a yellow solid and purified by chromatography on $SiO_2$ (eluent gradient 100% $CH_2Cl_2$ to 9:1 $CH_2Cl_2$-MeOH). The desired ether (5) was isolated as an off-white solid after triturating with diethyl ether: $R_f$ 0.28 (9:1 $CH_2Cl_2$-MeOH); UV $\lambda_{max}$ 215, 256 nm; LRMS (ESI$^+$) m/z 688.4 (M+H)$^+$, 711.4 (M+Na)$^+$; $^1$H NMR (DMSO-d$_6$) δ 10.02 (1H, s, PAB-NH), 8.10 (1H, d, J=7.2 Hz, amide NH), 7.81 (1H, d, J=9.0 Hz, amide NH), 7.56 (2H, d, J=8.7 Hz, PAB-CH×2), 7.21-7.39 (12H, m, aromatic), 5.98 (1H, t, J=5.1 Hz, cit-NH), 5.41 (2H, s, cit-NH$_2$), 5.03 (2H, s, Cbz-CH$_2$), 4.06-4.45 (4H, m, val-CH, Nor-CH, PAB-CH$_2$), 3.84-3.94 (2H, m, cit-CH, Nor-CH), 2.85-3.15 (2H, m, cit-CH$_2$), 1.87-2.04 (1H, m, val-CH), 1.67 (3H, s, Nor-Ac), 1.28-1.75 (4H, m, cit-CH$_2$'s), 0.98 (3H, d, J=6.6 Hz, Nor-CH$_3$), 0.86 (3H, d, J=6.6 Hz, val-CH$_3$), 0.82 (3H, d, J=6.9 Hz, val-CH$_3$).

Example 5

CBZ-VAL-CIT-PAB-O-ETOPOSIDE (6)

Following the Mitsunobu procedure described above, the pure fractions from chromatography on $SiO_2$ gave the ether as a white solid (64%); $R_f$ 0.29 (9:1 $CH_2Cl_2$-MeOH); UV $\lambda_{max}$ 215, 250, 290 nm; LRMS (ESI$^+$) m/z 1084.6 (M+H)$^+$, 1106.6 (M+Na)$^+$, 1122.6 (M+K)$^+$; $^1$H NMR (DMSO-d$_6$) δ 10.01 (1H, s, PAB-NH), 8.08 (1H, d, J=7.2 Hz, amide NH), 7.57 (2H, d, J=8.1 Hz, PAB-CH×2), 7.29-7.40 (7H, m, aromatic), 7.00 (2H, s, etop. aromatic), 6.53 (1H, s, etop. aromatic), 6.23 (2H, s, etop. aromatic), 6.01 (1H, d, J=3.3 Hz, etop-CH$_2$), 5.96 (1H, t, J=5.1 Hz, cit-NH), 5.40 (2H, s, cit-NH$_2$), 5.24 (1H, s, etop-OH), 5.22 (1H, s, etop-OH), 5.02 (2H, s, Cbz-CH$_2$), 4.92 (1H, d, J=3.0 Hz, etop-CH), 4.74 (2H, s, PAB-CH$_2$), 4.70 (1H, dd, J=9.9, 4.8 Hz, etop-CH), 4.56 (1H, d, J=7.8 Hz, etop-CH), 4.54 (1H, d, J=5.1 Hz, etop-CH), 4.36-4.44 (1H, m, val-CH), 4.25 (2H, dd, J=9.0 Hz, etop-CH×2), 4.06 (1H, dd, J=11.1, 4.8 Hz, etop-CH), 3.90 (1H, t, J=6.9 Hz, cit-CH), 3.62 (6H, s, etop-OCH$_3$×2), 3.49 (1H, t, J=9.6 Hz, etop-CH), 2.81-3.30 (9H, m, etop-CH×7, cit-NCH$_2$), 1.88-2.05 (1H, m, val-CH), 1.30-1.74 (4H, m, cit-CH$_2$'s), 1.22 (3H, d, J=4.8 Hz, etop-CH$_3$), 0.86 (3H, d, J=6.6 Hz, val-CH$_3$), 0.82 (3H, d, J=6.9 Hz, val-CH$_3$). Anal. (C$_{55}$H$_{65}$N$_5$O$_{18}$·2H$_2$O) C, H, N.

Example 6

CBZ-VAL-CIT-PAB-3'-O-COMBRETASTATIN A-4 (7)

Using the Mitsunobu reaction conditions described above, the compound was isolated as an amorphous solid after trituration ether. $R_f$ 0.42 (9:1 $CH_2Cl_2$-MeOH); mp 169-172 (dec); UV $\lambda_{max}$ 215, 248, 300 nm; LRMS (ESI$^+$) m/z 812.4 (M+H)$^+$, 834.4 (M+Na)$^+$, 850.4 (M+K)$^+$; $^1$H NMR (DMSO-d$_6$) δ 10.06 (1H, s, PAB-NH), 8.11 (1H, d, J=7.2 Hz, amide NH), 7.57 (2H, d, J=8.4 Hz, PAB-CH×2), 7.24-7.45 (6H, m, aromatic), 7.21 (2H, d, J=8.4 Hz, PAB-CH×2), 6.82-6.98 (2H, m, CSA4-H-5', 6'), 6.56 (2H, s, CSA4-H-2), 6.48 (2H, d, J=12.3 Hz, CSA4-cis-CH), 6.44 (2H, d, J=12.3 Hz, CSA4-cis-CH), 5.97 (1H, t, J=5.1 Hz, cit-NH), 5.41 (2H, s, cit-NH$_2$), 5.03 (2H, s, Cbz-CH$_2$), 4.76 (2H, s, PAB-CH$_2$), 4.36-4.45 (1H, m, val-CH), 3.92 (1H, t, J=7.2 Hz, cit-CH), 3.82 (3H, s, CSA4-3'-OCH$_3$), 3.61 (9H, s, CSA4-3,4,5-OCH$_3$), 2.88-3.07 (2H, m, cit-NCH$_2$), 1.90-2.03 (1H, m, val-CH), 1.28-1.78 (4H, m, cit-CH$_2$'s), 0.86 (3H, d, J=6.6 Hz, val-CH$_3$), 0.82 (3H, d, J=6.9 Hz, val-CH$_3$). Anal. (C$_{44}$H$_{53}$N$_5$O$_{10}$·H$_2$O) C, H, N.

Example 7

(1S, 2R)-N-ACETYL-O-(4-NITROPHENYLOXY-CARBONYL)NOREPHEDRINE (8)

Compound 4 (1.0 g, 5.17 mmol, 1.0 eq) and p-nitrophenyl-chloroformate (1.61 g, 7.76 mmol, 1.5 eq) were dissolved in anhydrous THF (12 mL, 0.5 M) while under N$_2$. Dry pyridine (0.63 mL, 7.76 mmol, 1.0 eq) was added via syringe over a 3 min period. The resulting turbid mixture contained no starting material after 15 min according to TLC (1:1 $CH_2Cl_2$-EtOAc). Solids were filtered off and washed with THF. The filtrate was concentrated to a yellow oil that was purified by chromatography on $SiO_2$ (1:1 hexanes-EtOAc). The desired product 8 was an off-white solid (1.43 g, 78%) that was stored in the dark at <0 C: $R_f$ 0.16 (1:1 hexanes-EtOAc); UV $\lambda_{max}$ 215, 270 nm; $^1$H NMR (CDCl$_3$) δ 8.24 (2H, d, J=9.3 Hz, Pnp-CH×2), 7.38 (2H, d, J=9.0 Hz, Pnp-CH×2), 7.32-7.44 (5H, m, aromatic), 5.78 (1H, d, J=3.3 Hz, H-1), 5.42 (1H, br d, J=8.4 Hz, NH), 4.61 (1H, dp, J=3.3, 7.2 Hz, H-2), 2.00(3H, s, Ac), 1.11 (3H, d, J=7.2 Hz, H-3).

Example 8

3'-O-(4-NITROPHENYLOXYCARBONYL)COMBRETASTATIN A-4 (9).

Using the same procedure as described above, combretastatin A-4 (120 mg, 0.38 mmol) was converted to the 4-nitrophenyl carbonate in quantitative yield (183 mg) and isolated as a yellow oil: $R_f$ 0.47 (3:2 hexanes-EtOAc); $^1$H NMR (CHCl$_3$) δ 8.30 (2H, d, J=9.3 Hz, Pnp-CH×2), 7.45 (2H, d, J=9.3 Hz, Pnp-CH×2), 7.18 (2H, d, J=1.5 Hz, H-2'), 6.88-6.94 (2H, m, H-5',6'), 6.51 (1H, d, J=12.0 Hz, cis-CH), 6.49 (2H, s, H-2), 6.48 (1H, d, J=12.0 Hz, cis-CH), 3.89 (3H, s, 3'-OCH$_3$), 3.84 (3H, s, 4-OCH$_3$), 3.70 (3H, s, 3,5-OCH$_3$).

Example 9

CBZ-VAL-CIT-PAB-OCO-(1S, 2R)-(N-ACETYL) NOREPHEDRINE (10)

The activated carbonate 8 (90 mg, 0.25 mmol) and Cbz-val-cit-PAB-OH 1 (130 mg, 0.25 mmol) were suspended in dry $CH_2Cl_2$ (8 mL), followed by the addition of DMAP (34 mg, 0.28 mmol, 1.1 eq). The reaction was stopped after 26 h by the addition of EtOAc and 10% citric acid. The layers were separated and the organic phase was further washed with water and brine. A precipitate formed that was filtered and added to the separated EtOAc layer and concentrated. The resulting yellow solid was subjected to chromatography on $SiO_2$ (gradient eluent 95:5 to 9:1 $CH_2Cl_2$-MeOH). The desired product eluted first and was concentrated to a white flaky solid (35 mg, 19%) while Cbz-val-cit-PAB-OH (1) was recovered as the second eluate: $R_f$ 0.17 (9:1 $CH_2Cl_2$-MeOH); UV $\lambda_{max}$ 215, 256 nm; LRMS (ESI$^+$) m/z 792.5 (M+H)$^+$, 814.5 (M+Na)$^+$, 830.4 (M+K)$^+$; $^1$H NMR (DMSO-d$_6$) δ 10.08 (1H, s, PAB-NH), 8.10 (1H, d, J=7.2 Hz, amide NH), 8.00 (1H, d, J=7.8 Hz, amide NH), 7.59 (2H, d, J=8.7 Hz, PAB-CH×2), 7.26-7.39 (10H, m, aromatic), 7.24 (2H, d, J=8.7 Hz, PAB-CH×2), 5.96 (1H, t, J=5.1 Hz, cit-NH), 5.61 (1H, d, J=4.2 Hz, Nor-CH), 5.40 (2H, s, cit-NH$_2$), 5.07 (2H, s, Cbz-CH$_2$), 5.03 (2H, s, PAB-CH$_2$), 4.40 (1H, dd, J=13.2, 7.8 Hz, val-CH), 4.03-4.14 (1H, m, Nor-CH), 3.92 (1H, t, J=7.8 Hz, cit-CH), 2.85-3.06 (2H, m, cit-CH$_2$), 1.90-2.02 (1H, m, val-CH), 1.74 (3H, s, Nor-Ac), 1.28-1.75 (4H, m, cit-CH$_2$'s), 0.96 (3H, d, J=6.9 Hz, Nor-CH$_3$), 0.87 (3H, d, J=6.9 Hz, val-CH$_3$), 0.83 (3H, d, J=7.2 Hz, val-CH$_3$). Anal. (C$_{38}$H$_{48}$N$_6$O$_9$·½H$_2$O) C, H, N.

Example 10

CBZ-VAL-CIT-PAB-OCO-COMBRETASTATIN A-4 (11)

Activated combretastatin A-4 9 (120 mg, 0.25 mmol) and Cbz-val-cit-PAB-OH 1 (130 mg, 0.25 mmol) were suspended in dry CH$_2$Cl$_2$/pyridine (3 mL each) followed by the addition of DMAP (34 mg, 0.28 mmol, 1.1 eq). The reaction was sonicated for 2 h followed by stirring for 20 h. Evaporation of the reaction mixture followed by purification by chromatography on SiO$_2$ (gradient eluent 100% CH$_2$Cl$_2$ to 9:1 CH$_2$Cl$_2$-MeOH), and concentration of the appropriate fractions resulted in a yellow oil that was precipitated from CH$_2$Cl$_2$ (1 mL) through the addition of ether. This led to a yellow solid (83 mg, 38%): R$_f$ 0.47 (9:1 CH$_2$Cl$_2$-MeOH); mp 155-158 (dec); UV $\lambda_{max}$ 215, 245, 285 nm; LRMS (ESI$^+$) m/z 856.5 (M+H)$^+$, 878.5 (M+Na)$^+$, 894.5 (M+K)$^+$; $^1$H NMR (DMSO-d$_6$) δ 10.10 (1H, s, PAB-NH), 8.11 (1H, d, J=7.8 Hz, amide NH), 7.62 (2H, d, J=8.1 Hz, PAB-CH×2), 7.25-7.40 (8H, m, aromatic), 7.15 (1H, dd, J=8.7, 1.8 Hz, CSA4-H-6'), 7.07 (1H, d, J=8.1 Hz, CSA4-H-5'), 7.06 (1H, d, J=2.4 Hz, CSA4-H-2'), 6.51 (2H, s, CSA4-H-2), 6.48 (2H, s, CSA4-CH=CH), 5.97 (1H, t, J=5.1 Hz, cit-NH), 5.42 (2H, s, cit-NH$_2$), 5.14 (2H, s, Cbz-CH$_2$), 5.02 (2H, s, PAB-CH$_2$), 4.40 (1H, dd, J=12.9, 8.1 Hz, val-CH), 3.92 (1H, t, J=7.2 Hz, cit-CH), 3.73 (3H, s, CSA4-3'-OCH$_3$), 3.61 (3H, s, CSA4-4-OCH$_3$), 3.58 (6H, s, CSA4-3,5-OCH$_3$), 2.88-3.07 (2H, m, cit-NCH$_2$), 1.88-2.04 (1H, m, val-CH), 1.28-1.178 (4H, m, cit-CH$_2$'s), 0.86 (3H, d, J=6.9 Hz, val-CH$_3$), 0.82 (3H, d, J=6.6 Hz, val-CH$_3$). Anal. (C$_{45}$H$_{53}$N$_5$O$_{12}$·H$_2$O) C, H, N.

Example 11

General Procedure for Cathepsin B Assays.

Bovine spleen cathepsin B (Sigma-Aldrich), dissolved in phosphate buffered saline (pH 7.2, 1 mg/mL final concentration), was activated as previously described (Bajkowski, A. S.; Frankfater, A. Specific Spectrophotometric Assays for Cathepsin B. *Anal. Biochem.* 1975, 68, 119-127). A 1.0 mM stock solution of the peptide substrate in DMSO was added to acetate buffer (25 mM) containing 1 mM EDTA (pH 5.1) to give a final concentration of 0.08-0.14 mM, and to this was added the activated enzyme (12-15 μg/mL). In the case of the naphthol ether 2, a 5.0 mM solution in MeOH was diluted to a final concentration of 0.22 mM. Periodically, aliquots were taken, quenched with an equal volume of MeCN, centrifuged, and 100 μL injections analyzed by HPLC (4.6 mm×15 cm C$_{18}$ column) with detection between 210 and 400 nm. The mobile phase consisted of (A) 5 mM sodium phosphate (pH 7) and (B) either MeOH (for compounds 2, 7, and 11) or MeCN (for compounds 5, 6, and 10). The gradient elution was 90% to 10% A over 10 min, followed by 5 min at 10% A, and the flow rate was 1.0 mL/min. The disappearance of substrate and the appearances of released alcohol and Cbz-val-cit were recorded. Cathepsin B hydrolysis rates were calculated according to the disappearance of substrate (Table 7).

TABLE 7

| Com-pound | Stability[a] | | | Specific activity of cathepsin B[b] |
|---|---|---|---|---|
| | pH 5.1 | pH 7.2 | Human serum | |
| 2 | 0% loss, 7 days | 0% loss, 7 days | 0% loss, 7 days | 350 nmol/min/mg |
| 5 | 0% loss 7 d | 0% loss 7 d | 0% loss 7 d | 145 nmol/min/mg[c] |
| 6 | 0% loss, 7 days | 0% loss, 7 days | t½ 48 hours[d] | 160 nmol/min/mg |
| 7 | 0% loss, 7 days | 0% loss, 7 days | 0% loss, 7 days | 61 nmol/min/mg |
| 10 | t½ 104 hours | t½ 79 hours | t½ 9 days | 150 nmol/min/mg |
| 11 | t½ 62 hours | t½ 55 hours | t½ 45 hours | 32 nmol/min/mg |

[a] measured as the loss of starting material and the appearance of the released alcohol at 37° C. in phosphate buffered saline at pH 7.2, acetate buffer at pH 5.1, or in pooled serum.
[b] measured as the loss of starting material at 37° C. in pH 5.1 acetate buffer.
[c] measured as the loss of starting material, which correlated to the appearance of Z-val-cit-COOH. HPLC analysis indicated that N-acetylnorephedrine
[d] Etoposide (VIIIa) and the etoposide moiety of 6 were unstable in serum. There was no apparent breakdown of the peptide-linker in 6. No Cbz-val-cit-COOH, 1, or VIIIa were detected.

General Procedure for All Stability Studies.

Solutions of the substrates (0.08-0.14 mM in DMSO, and 0.22 mM in MeOH for 2) were diluted 10-20-fold in PBS, acetate buffer (25 mM, pH 5.1), or pooled human serum, and incubation was carried out at 37° C. For the serum studies, equal volumes of MeCN were added and the samples were centrifuged prior to HPLC analysis. The other samples were injected directly into the HPLC.

In vitro Cytotoxicity Assays.

L2987 human lung adenocarcinoma cells were obtained as previously described (Svensson, H. P.; Vrudhula, V. M.; Emsweiler, J. E.; MacMaster, J. F.; Cosand, W. L.; Senter, P. D.; Wallace, P. M. In Vitro and In Vivo Activities of a Doxorubicin Prodrug in Combination with Monoclonal Antibody β-Lactamase Conjugates. *Cancer Res.* 1995, 55, 2357-2365). WM266/4 and IGR-39 human melanoma cells were obtained from ATCC (Manassas, Va.) and DSMZ (Braunschweig, Germany), respectively. L2987 and WM266/4 cells were grown in Roswell Park Memorial Institute (RPMI) medium containing 10% fetal bovine serum and 10U/mL penicillin G and 10 μg/mL streptomycin sulfate. Dulbecco's modified Eagle's medium was used in place of RPMI for the IGR-39 cells. The cells (2,500 cells in 0.1 mL medium) were plated into 96-well plates, and after 24 h at 37° C., various concentrations of the drugs in medium (50 μL) were added in triplicate. Incubation was continued for an additional 24 h, the cultures were washed, and fresh medium (0.15 mL) was added. After 48 h at 37° C., [$^3$H] thymidine (25 μL, 0.5 μCi/well) was added, and the cultures were frozen and harvested 4 h later. Incorporation of label was measured using a β-counter.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A compound of the formula:

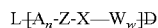

wherein:
D is a drug moiety;
L is a ligand;
A is an optional acyl unit;
Z is an amino acid or a peptide;
X is an aminobenzyl ether self-immolative group;
W is an optional second self-immolative group;
n is an integer of 0 or 1;
w is an integer of 0 or 1; and
wherein X forms an ether linkage with W when w is 1 or with D when w is 0.

2. A compound of claim 1, represented by the following formula:

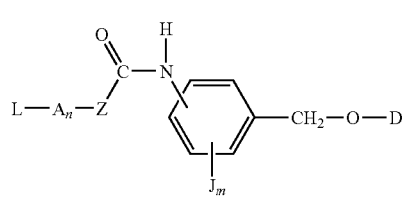

wherein:
—O-D is a portion of a drug, where the drug has the formula HO-D;
J is a substituent group, and m is 0, 1, 2, 3 or 4;

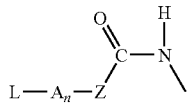

is situated at an ortho- or para- position with respect to the —CH$_2$— group;
Z-C(=O) is an amino acid or a peptide;
A is an acyl unit where n is 0 or 1; and
L is a ligand.

3. A compound of claim 1, represented by the following formula:

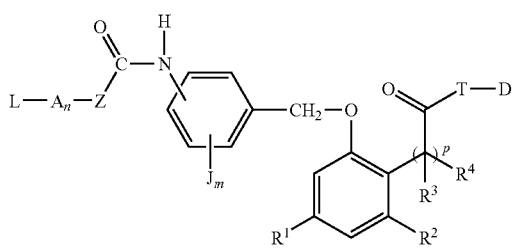

wherein:
T-D is a portion of a drug, where the drug has the formula HT-D;
T is O, S, NH, or N(lower alkyl);
J is a substituent group, and m is 0, 1, 2; 3 or 4;

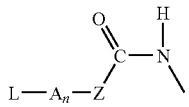

is situated at an ortho- or para- position with respect to the —CH$_2$— group;

Z-C(=O) is an amino acid or a peptide;

A is an acyl unit and n is 0 or 1;

L is a ligand;

p is 1 or 2; and each of $R^1$, $R^2$, $R^3$ and $R^4$ is independently selected from H and $C_1$-$C_5$ alkyl.

4. A compound of claim 2 wherein the O of —O-D is bonded to a carbon that forms an aromatic ring of D.

5. A compound of claim 4 wherein the drug is 1,2,9,9a-tetra-hydro-cyclo-propa[c]benz[e]indol-4-one (CBI) conjugated to a minor groove binder.

6. A compound of claim 4 wherein the drug is cyclopropapyrroloindole (CPI) conjugated to a minor groove binder.

7. A compound of claim 4 wherein the drug is 1,2,9,9a-tetra-hydro-cyclo-propa[c]pyrido[3,2-e]indol-4-one (CPyI) conjugated to a minor groove binder.

8. A compound of claim 4 wherein the drug is selected from:
U-76,073; seco-adozelesin; bizelesin; 1,2,9,9a-tetra-hydro-cyclo-propa[c]benz[e]indol-4-one-trimethoxyindole (CBI-TMI); duocarmycin C2; duocarmycin B2; seco-CC-1065; pancratistatin; carminomycin; streptonigrin; zorubicin; elliptinium acetate; mitoxantrone; daunorubicin; phenol mustard; doxorubicin; etoposide, combretastatin A-4, and 7-ethyl-10-hydroxycamptothecin (SN-38).

9. A compound of claim 2 wherein the O of —O-D is bonded to an aliphatic carbon of D.

10. A compound of claim 9 in which the drug is auristatin E.

11. A compound of claim 2 wherein the H of H—O-D has a pKa of 16 or less.

12. A compound of claim 3 wherein T is NH or N(lower alkyl).

13. A compound of claim 3 wherein T is O or S.

14. A compound of claim 12 wherein the drug is selected from 5-amino-1,2,9,9a-tetra-hydro-cyclopropa[c]benz[e]indol-4-one (CBI) conjugated to a minor groove binder; 5-amino-cyclopropapyrroloindole (CPI) conjugated to a minor groove binder; and 5-amino-1,2,9,9a-tetra-hydro-cyclopropa[c]pyrido[3,2-e]indol-4-one (CPyI) conjugated to a minor groove binder.

15. A compound of claim 12 wherein the drug is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.

16. A compound of claim 13 wherein the drug is auristatin E.

17. A compound of claim 13 wherein the drug is a hydroxyl containing drug moiety selected from the group consisting of: etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin, N-(5,5-diacetoxypentyl)doxorubicin, vincristine, vinblastine and derivatives thereof.

18. A compound of claim 13 wherein the drug is a sulfhydryl-containing moiety selected from the group consisting of esperamicin, 6-mercaptopurine, and derivatives thereof.

19. A compound of claim 2 wherein L is an immunoglobulin, or an antigen-binding fragment thereof.

20. A compound of claim 3 wherein L is an immunoglobulin, or an antigen-binding fragment thereof.

21. A compound of claim 19 wherein L is an mAb selected from the group consisting of BR96, L6, trastuzumab, rituximab, S2C6, AC10, and antigen-binding fragments thereof.

22. A compound of claim 20 wherein L is an mAb selected from the group consisting of BR96, L6, trastuzumab, rituximab, S2C6, AC10, and antigen-binding fragments thereof.

23. A compound of claim 2 wherein L is selected from the group consisting of bombesin, EGF, transferrin, gastrin, gastrin-releasing peptide, platelet-derived growth factor, IL-2, IL-6, TFG-α, TFG-β, VGF, insulin and insulin-like growth factors I and II, carbohydrates, lectins, and apoprotein from low-density lipoproteins.

24. A compound of claim 3 wherein L is selected from the group consisting of bombesin, EGF, transferrin, gastrin, gastrin-releasing peptide, platelet-derived growth factor, IL-2, IL-6, TFG-α, TFG-β, VGF, insulin and insulin-like growth factors I and II, carbohydrates, lectins, and apoprotein from low-density lipoproteins.

25. A compound of claim 2 wherein L is selected from the group consisting of poly(ethylene glycol); poly(propylene glycol); (hydroxypropyl)methacrylamide; chitins; dextrans; styrene-co-maleic acid/anhydride, polyglutamic acid and polylysine.

26. A compound of claim 3 wherein L is selected from the group consisting of poly(ethylene glycol); poly(propylene glycol); (hydroxypropyl)methacrylamide; chitins; dextrans; styrene-co-maleic acid/anhydride, polyglutamic acid and polylysine.

27. A compound of claim 2 wherein m is 0.

28. A compound of claim 3 wherein m is 0.

29. A compound of claim 2 wherein m is 1 and the substituent is an electron-withdrawing group selected from F, Cl, Br, CN, CF$_3$, CONH$_2$, CHO, CO$_2$CH$_3$, COCH$_3$, NHCOCH$_3$, NO$_2$, and sulfonyl groups.

30. A compound of claim 3 wherein m is 1 and the substituent is an electron-withdrawing group selected from F, Cl, Br, CN, CF$_3$, CONH$_2$, CHO, CO$_2$CH$_3$, COCH$_3$, NHCOCH$_3$, NO$_2$, and sulfonyl groups.

31. A compound of claim 2 wherein Z is a dipeptide or a tripeptide.

32. A compound of claim 3 wherein Z is a dipeptide or a tripeptide.

33. A compound of claim 2 wherein Z is valine-citrulline.

34. A compound of claim 3 wherein Z is valine-citrulline.

35. A compound of claim 2 wherein Z is phenylalanine-lysine.

36. A compound of claim 3 wherein Z is phenylalanine-lysine.

37. A compound of claim 2 wherein $$L-A_n-Z-\overset{O}{\underset{}{C}}-\overset{H}{\underset{}{N}}-$$

situated at the para- position with respect to the —CH2— group.

38. A compound of claim 3 wherein $$L-A_n-Z-\overset{O}{\underset{}{C}}-\overset{H}{\underset{}{N}}-$$

is situated at the para- position with respect to the —CH$_2$— group.

39. A compound of claim 2 wherein n is 1.

40. A compound of claim 3 wherein n is 1.

41. A compound of claim 39 wherein A is

[structure: succinimide-N-(CH$_2$)$_q$-C(O)-]

and q is 1-10.

42. A compound of claim 40 wherein A is

[structure: succinimide-N-(CH$_2$)$_q$-C(O)-]

and q is 1-10.

43. A compound of claim 41 where q=5.

44. A compound of claim 42 where q=5.

45. A pharmaceutical composition comprising a therapeutically effective amount of a compound of claim 1 and a pharmaceutically acceptable carrier, diluent or excipient.

46. A pharmaceutical composition comprising a therapeutically effective amount of a compound of claim 2 and a pharmaceutically acceptable carrier, diluent or excipient.

47. A pharmaceutical composition comprising a therapeutically effective amount of a compound of claim 3 and a pharmaceutically acceptable carrier, diluent or excipient.

48. The compound of claim 1 wherein:

D is

[structure: pyrroloquinoline with CH$_2$Cl, OH, N—MGB substituents]

L is cAC10;

A is an optional acyl unit;

Z is -val-lys-;

X is

[structure: -HN-phenyl-CH$_2$-O-]

W is an optional second self-immolative group;

n is an integer of 0 or 1;

w is an integer of 0 or 1; and

MGB is a DNA minor groove binder.

49. The compound of claim 48 wherein

L is cAC10;

A is

[structure: maleimide-(CH$_2$)$_5$-C(O)-NH-CH$_2$CH$_2$-O-CH$_2$CH$_2$-O-CH$_2$CH$_2$-O-CH$_2$CH$_2$CH$_3$]

and w is 0.

50. The compound of claim 49 having the formula

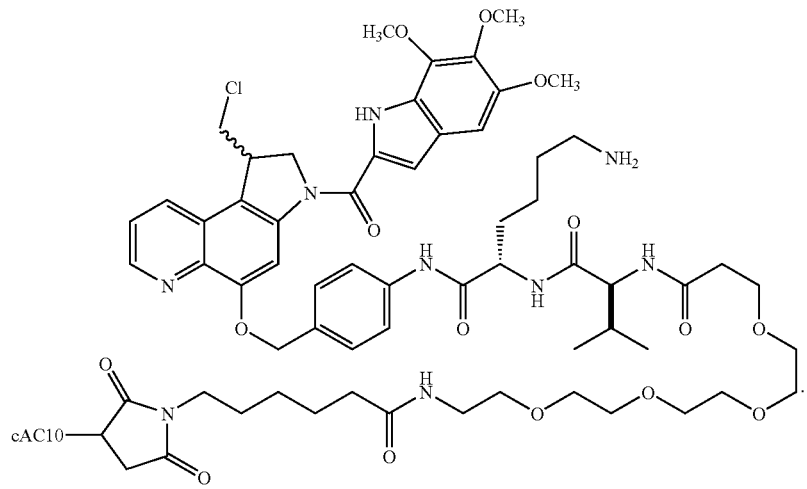

51. The compound of claim 48 wherein MGB is (S)-N-[2-[[1-(chloromethyl)-1,6-dihydro-5-hydroxy-8-methylbenzo[1,2-b:4,3-b']dipyrrol-3(2-yl]carbonyl]-1H-indol-5-yl]-6-(diethylamino)-2-benzofurancarboxamide(U-76,073); seco-adozelesin; bizelesin; 1,2,9,9a-tetra-hydro-cyclo-propa[c]benz[e]indol-4-one-trimethoxyindole (CBI-TMI); duocarmycin C2; duocarmycin B2; or benzo(1,2-b:4,3-b')dipyrrole-3(2H)-carboxamide, 7-((1,6-dihydro-4-hydroxy-5-methoxy-7-((4,5,8,8a-tetrahydro-7-methyl-4-oxocyclopropa©pyrrolo(3,2-e)indol-2-(1H)-yl)carbonyl)benzo(1,2-b:4,3-b')dipyrrol-3(2H)-yl)carbonyl)-1,6-dihydro-4-hydroxy-5-methoxy-,(7bR)(seco-CC-1065).

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Description of Artificial Sequence: Possible
      form of Peptide Z described herein

<400> SEQUENCE: 1

Gly Phe Leu Gly
1

<210> SEQ ID NO 2
<211> LENGTH: 4
<212> TYPE: PRT
<213> ORGANISM: Artificial
<220> FEATURE:
<223> OTHER INFORMATION: Description of Artificial Sequence: Possible
      form of Peptide Z described herein

<400> SEQUENCE: 2

Ala Leu Ala Leu
1